United States Patent
Greco et al.

(10) Patent No.: US 11,352,341 B2
(45) Date of Patent: Jun. 7, 2022

(54) 2H-INDAZOLE DERIVATIVES AS CDK4 AND CDK6 INHIBITORS AND THERAPEUTIC USES THEREOF

(71) Applicant: Beta Pharma, Inc., Wilmington, DE (US)

(72) Inventors: Michael Nicholas Greco, Lansdale, PA (US); Michael John Costanzo, Warminster, PA (US); Jirong Peng, Mequon, WI (US); Don Zhang, Princeton, NJ (US)

(73) Assignee: BETA PHARMA, INC., Wilmington, DE (US)

( * ) Notice: Subject to any disclaimer, the term of this patent is extended or adjusted under 35 U.S.C. 154(b) by 1 day.

(21) Appl. No.: 16/965,376

(22) PCT Filed: Jan. 29, 2019

(86) PCT No.: PCT/US2019/015547
§ 371 (c)(1),
(2) Date: Jul. 28, 2020

(87) PCT Pub. No.: WO2019/148161
PCT Pub. Date: Aug. 1, 2019

(65) Prior Publication Data
US 2021/0139459 A1    May 13, 2021

Related U.S. Application Data

(60) Provisional application No. 62/623,516, filed on Jan. 29, 2018.

(51) Int. Cl.
*C07D 401/14* (2006.01)
*A61K 45/06* (2006.01)

(52) U.S. Cl.
CPC ............ *C07D 401/14* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 9,878,994 B2* | 1/2018 | Greco | A61K 45/06 |
| 2005/0059670 A1 | 3/2005 | Beylin et al. | |
| 2010/0160340 A1 | 6/2010 | Coates et al. | |
| 2011/0009353 A1 | 1/2011 | Chen-Kiang et al. | |
| 2017/0210726 A1 | 7/2017 | Greco et al. | |

FOREIGN PATENT DOCUMENTS

| | | |
|---|---|---|
| WO | 2003/062236 A1 | 7/2003 |
| WO | 2007/140222 A2 | 12/2007 |
| WO | 2016/014904 A1 | 1/2016 |

OTHER PUBLICATIONS

International Search Report and Written Opion dated Mar. 26, 2019 in Application No. PCT/US2019/015547.

* cited by examiner

*Primary Examiner* — Heidi Reese
(74) *Attorney, Agent, or Firm* — Cantor Colburn LLP

(57) ABSTRACT

2-Aminopyrimidine-substituted 2H-indazole compounds of formula (I), where $R^1$ is hydrogen, and their prodrugs, where $R^1$ is a metabolizable group under physiological conditions, as cyclin-dependent kinase (CDK) and cell-proliferation inhibitors, and therapeutic uses and methods of preparation thereof, are disclosed. These compounds, and pharmaceutically acceptable salts, solvates, prodrugs, and pharmaceutical compositions thereof, are useful for treating diseases and disorders associated with activity of cyclin-dependent kinases, in particular CDK4/6, including but not limited to various cancers and inflammation-related diseases or conditions.

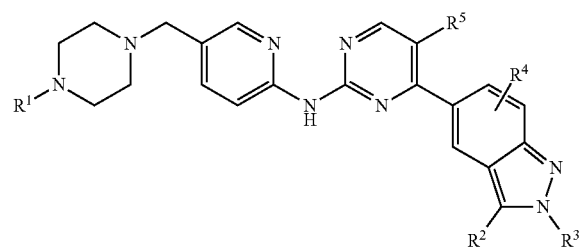

(I)

19 Claims, No Drawings

2H-INDAZOLE DERIVATIVES AS CDK4 AND CDK6 INHIBITORS AND THERAPEUTIC USES THEREOF

CROSS-REFERENCE TO RELATED APPLICATIONS

This application is a U.S. national phase application of International Application No. PCT/US2019/015547, filed on Jan. 29, 2019, which claims priority under 35 U.S.C. § 119(e) to U.S. Provisional Patent Application No. 62/623,516, filed on Jan. 29, 2018, the disclosures of which are fully incorporated herein by reference in their entireties.

FIELD OF THE INVENTION

The present invention is related to the field of compounds, compositions and methods for the treatment or prevention of a disease, disorder, or medical condition mediated through certain cyclin-dependent kinases (CDKs), especially CDK4 and CDK6. The diseases include various cancers.

BACKGROUND OF THE INVENTION

Cyclin-dependent kinases are a family of protein kinases that regulate cell division and proliferation. Cell cycle progression is controlled by cyclins and their associated cyclin-dependent kinases, such as CDK1, CDK2, CDK3, CDK4 and CDK6, while other CDKs such as CDK7, CDK8 and CDK9 are critical to transcription. CDK binding to cyclins forms heterodimeric complexes that phosphorylate their substrates on serine and threonine residues, which in turn initiates events required for cell-cycle transcription and progression. Since uncontrolled cell proliferation is a hallmark of cancer, and most cancer cells exhibit deregulation of CDKs, inhibition of CDKs has emerged as a potential treatment for various cancers. Inhibitors with varying degrees of selectivity for CDKs have been reported; however, selective CDK4/6 inhibitors are currently viewed as a promising class of potential anticancer or anti-inflammatory agents due to both the critical role of CDK4/6 in regulating cell proliferation and the toxic effects associated with inhibition of other members of the CDK family.

Recently, several types of aminopyrimidine derivatives have been reported to be selective CDK4/6 inhibitors. See, e.g., WO 2003/062236, WO 2007/140222, and US 2010/0160340. Each of these types of molecules contains a 2-aminopyrimidine moiety bound through the 2-amino group to an aryl or heteroaryl ring system. There remains a need to develop new CDK4/6 inhibitors as novel anticancer and/or anti-inflammatory agents.

SUMMARY OF THE INVENTION

The present invention relates to 2-aminopyrimidine-substituted 2H-indazole derivatives, in which the 2-amino group is substituted by a 5-(piperazin-1-ylmethyl)pyridin-2-yl) group, and the 4-N position of the piperazine moiety is unsubstituted or substituted by a metabolizable group that can be hydrolyzed under physiological conditions. These compounds are effective as selective CDK inhibitors and useful in the treatment or prevention of diseases, disorders, or medical conditions mediated through certain CDKs, in particular CDK4 and CDK6, such as various types of cancers and inflammation-related conditions. The compounds comprising a metabolizable group on the piperazine moiety can serve as more targeted therapeutic agents under controlled release.

One aspect of the present invention is directed to a compound of formula (I):

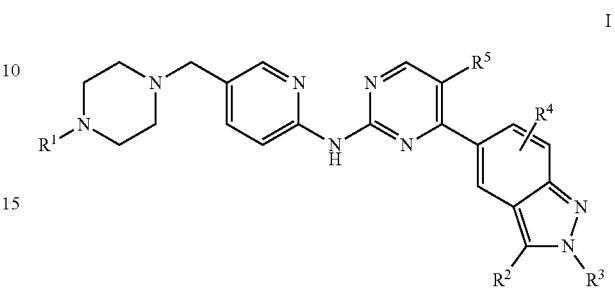

or a pharmaceutically acceptable salt, solvate, or prodrug thereof, wherein:

$R^1$ is hydrogen or a metabolizable group that can be removed under physiological conditions to form the corresponding unsubstituted compound, wherein the metabolizable group is selected from, but not limited to, —C(O)R, wherein R is H, $C_1$-$C_8$ alkyl or $C_3$-$C_7$ cycloalkyl, each (except hydrogen) optionally substituted, and —C(O)OR', wherein R' is $C_1$-$C_8$ alkyl or $C_3$-$C_7$ cycloalkyl each optionally substituted;

$R^2$ is selected from the group consisting of $C_1$-$C_6$ alkyl, $C_3$-$C_6$ cycloalkyl, and cycloalkylmethyl;

$R^3$ is hydrogen or $C_1$-$C_6$ alkyl;

$R^4$ is hydrogen, halogen, or $C_1$-$C_6$ alkyl; and $R^5$ is hydrogen or halogen.

Another aspect of the present invention is directed to a pharmaceutical composition comprising a compound of formula (I), or a pharmaceutically acceptable salt or solvate thereof, and one or more pharmaceutically acceptable excipients, such as adjuvants, diluents, and/or carriers.

Another aspect of the present invention is directed to a method of treating a disease, disorder, or condition mediated through at least one of cyclin-dependent kinases (CDK), in particular CDK4, CDK6, or a combination thereof, comprising administering to a subject in need thereof a therapeutically effective amount of a compound of formula (I), or a pharmaceutically acceptable salt or solvate thereof.

Another aspect of the present invention is directed to a method of treating a disease, disorder, or condition mediated through at least one of cyclin-dependent kinases (CDK), in particular CDK4, CDK6, or a combination thereof, comprising administering to a subject in need thereof a therapeutically effective amount of a pharmaceutical composition comprising a compound of formula (I), or a pharmaceutically acceptable salt or solvate thereof, and one or more pharmaceutically acceptable excipients, such as adjuvants, diluents, and/or carriers.

In one embodiment, the diseases, disorders, or conditions associated with one or more cyclin-dependent kinases, in particular CDK4, CDK6, or a combination thereof, comprise cancers, which may include, but are not limited to, lung cancer, especially non-small cell lung cancer (NSCLC), breast cancer, prostate cancer, colorectal cancer, glioblastoma, mantel cell lymphoma, chronic myeloid leukemia and acute myeloid leukemia, and complications thereof. In another embodiment, the diseases, disorders, or conditions comprise the inflammation-related diseases and conditions, such as arthritis, e.g., rheumatic arthritis, and cystic fibrosis.

Another aspect of the invention is directed to a method of inhibiting cell proliferation comprising treating the cells with an effective amount of a compound of formula (I), or a salt, solvate, or composition thereof.

Another aspect of the invention is directed to a method of inhibiting a cyclin-dependent kinase (CDK), in particular CDK4, CDK6, or a combination thereof, comprising treating the kinase with an effective amount of a compound of formula (I), or a salt, solvate, or composition thereof.

Another aspect of the present invention is directed to use of the compounds of this invention for the study of CDKs in biological and pathological phenomena and for comparative evaluation of new kinase inhibitors.

Another aspect of the present invention is directed to use of a compound of formula (I) according to any embodiments described herein, or a pharmaceutically acceptable salt, solvate, or composition thereof, in the manufacture of a medicament for treatment of a disease or disorder associated with a CDK activity. The CDK activity is preferably activity of CDK4, CDK6, or a combination thereof.

Still another aspect of the present invention is directed to the methods of synthesizing the compounds of formula (I) as substantially disclosed and described herein.

Other aspects or advantages of the present invention will be apparent to those skilled in the art in view of the following detailed description and claims in combination with the knowledge and skills generally known in the field.

DETAILED DESCRIPTION OF THE INVENTION

In a prior patent application the applicant has disclosed a new class of compounds having a core structure of formula (II) containing the piperazine-pyridine-NH-pyrimidine-indazole motif, namely the 4-(2H-indazol-5-yl)-N-(5-(piperazin-1-ylmethyl)pyridin-2-yl)pyrimidin-2-amine core, useful as CDK, in particular CDK4 and CDK6, inhibitors. See US 2017/0210726, which is incorporated herein by reference in its entirety.

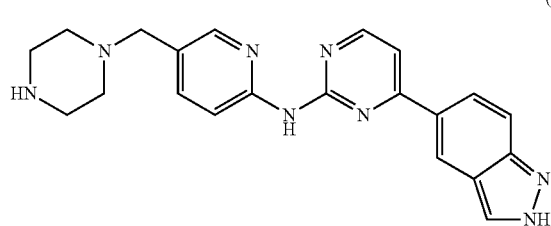

(II)

All the preferred compounds of this class reported previously contain substituents on the indazole and piperazine moieties as shown in formula (I) below. In particular, the nitrogen (N) at position 4 of the piperazine moiety contains a substituent ($R^1$ in formula I) such as $C_1$-$C_3$ alkyl, preferably ethyl group. The present invention is based on a discovery that the compounds with the piperazine moiety unsubstituted at the 4-position are also active inhibitors of CDK4 and CDK6. This discovery significantly expands the pool of compounds that can serve as potential therapeutic agents for treatment of CDK4 and CDK6 related diseases and disorders, because numerous prodrugs may be designed, including those disclosed in the present application, that may have various advantages in the targeted delivery and/or controlled release.

In one aspect, the present invention provides a compound of formula (I):

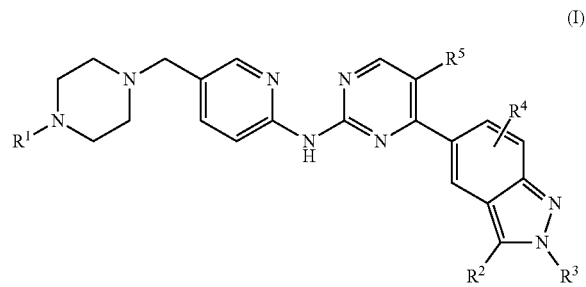

(I)

or a pharmaceutically acceptable salt, solvate, or prodrug thereof, wherein:

$R^1$ is hydrogen or a metabolizable group (prodrugs) that can be removed under physiological conditions to form the corresponding unsubstituted compound;

$R^2$ is selected from the group consisting of hydrogen, $C_1$-$C_6$ alkyl, $C_3$-$C_6$ cycloalkyl, and $C_3$-$C_6$ cycloalkylmethyl;

$R^3$ is hydrogen or $C_1$-$C_6$ alkyl;

$R^4$ is hydrogen, halogen, or $C_1$-$C_6$ alkyl; and $R^5$ is hydrogen or halogen.

In one embodiment of this aspect, $R^1$ is hydrogen.

In another embodiment of this aspect, $R^1$ is a metabolizable group that can be removed under physiological conditions to form the corresponding unsubstituted compound.

In some embodiments, the metabolizable group is RC(O)—, wherein R is $C_1$-$C_8$ alkyl or $C_3$-$C_7$ cycloalkyl. In some embodiments, R is selected from, but is not limited to, H, methyl, ethyl, propyl, isopropyl, or the like, preferably, methyl or ethyl, and more preferably methyl.

In some embodiments, the metabolizable group is R'OC(O)—, wherein R' includes, but is not limited to, methyl, ethyl, propyl, isopropyl, cyclopropyl, or the like, preferably, methyl or ethyl, and more preferably methyl.

In another embodiment of this aspect, $R^2$ is $C_1$-$C_6$ alkyl, $C_3$-$C_6$ cycloalkyl, or $C_3$-$C_6$ cycloalkylmethyl.

In another embodiment of this aspect, $R^2$ is methyl, ethyl, propyl, isopropyl, cyclopropyl, cyclopentyl, cyclopropylmethyl, or cyclopentylmethyl.

In another embodiment of this aspect, $R^3$ is $C_1$-$C_6$ alkyl.

In another embodiment of this aspect, $R^3$ is methyl, ethyl, propyl, or isopropyl.

In certain embodiments, the present invention provides a compound of formula (I), wherein the $R^4$ substituent is attached at the 7-position of the indazole moiety, characterized by formula (Ia):

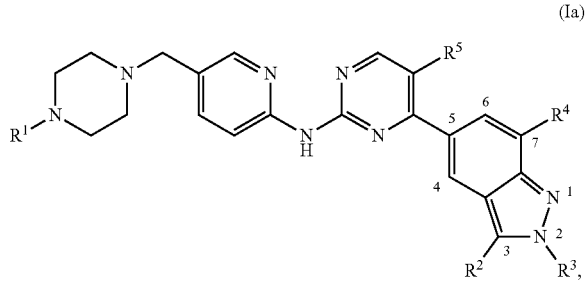

(Ia)

or a pharmaceutically acceptable salt, solvate, or prodrug thereof, wherein:

$R^1$ is hydrogen or RC(O)—, wherein R is hydrogen or $C_1$-$C_6$ alkyl;

$R^2$ is selected from the group consisting of hydrogen, $C_1$-$C_6$ alkyl, $C_3$-$C_6$ cycloalkyl, and cycloalkylmethyl;

$R^3$ is hydrogen or $C_1$-$C_6$ alkyl;

$R^4$ is hydrogen or halogen; and $R^5$ is hydrogen or halogen.

In another embodiment of this aspect, $R^4$ is hydrogen or fluoro.

In another embodiment of this aspect, $R^5$ is hydrogen or fluoro.

In another embodiment of this aspect, $R^1$ is hydrogen; $R^2$ is isopropyl, cyclopropyl, cyclopropylmethyl, or cyclopentyl; $R^3$ is methyl or ethyl, $R^4$ is hydrogen or fluoro, and $R^5$ is hydrogen or fluoro.

In certain preferred embodiments of this aspect, the $R^4$ substituent is attached at the 7-position of the indazole moiety, and $R^5$ is fluoro, characterized by formula (Ib):

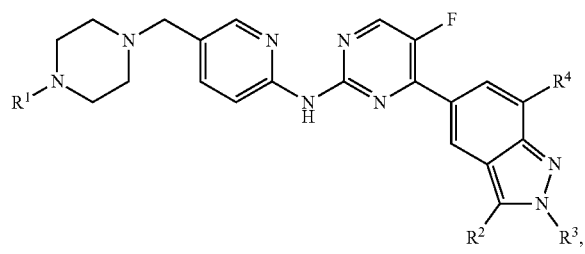

(Ib)

wherein $R^4$ is preferably hydrogen or halogen; and when $R^4$ is a halogen, it is preferably chloro (Cl) or fluoro (F), more preferably fluoro (F); and wherein $R^1$, $R^2$, and $R^3$ are each defined in any of the embodiments described here.

In certain preferred embodiments of this aspect, the present invention provides a compound of formula selected from the group consisting of:

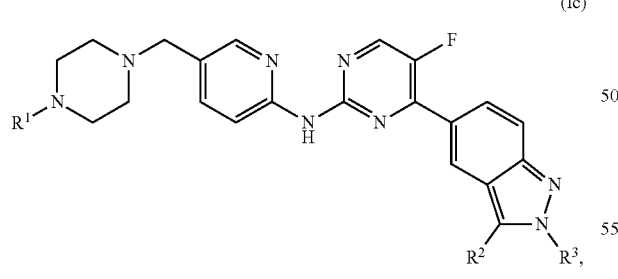

(Ic)

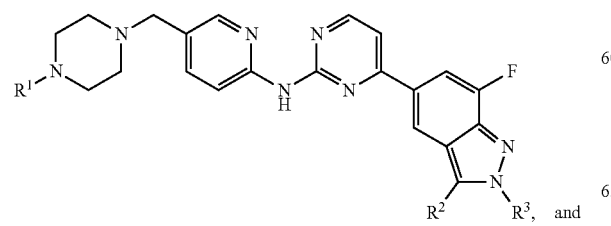

(Id)

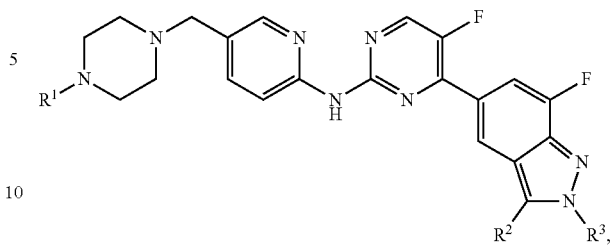

(Ie)

or a pharmaceutically acceptable salt, solvate, or prodrug thereof, wherein $R^1$, $R^2$, and $R^3$ are each defined in any of the embodiments described here.

With regard to the compounds of any of formula I, Ia, Ib, Ic, Id, or Ie, the present invention encompasses any and all possible combinations of the embodiments described herein so long as such combinations would provide stable compounds.

In certain preferred embodiments of this aspect, the present invention provides the compounds listed in Table 1 (infra), and pharmaceutically acceptable salts, solvates, and prodrugs thereof.

In a preferred embodiment, the present invention provides a compound selected from the group consisting of:

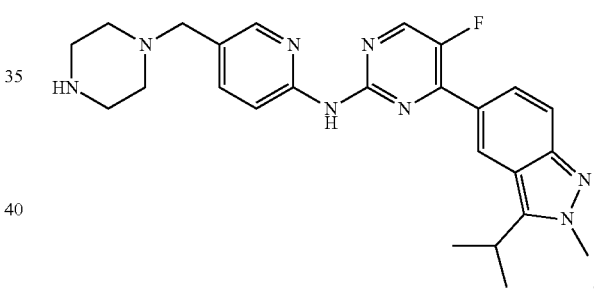

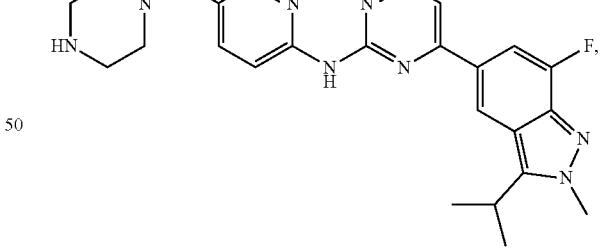

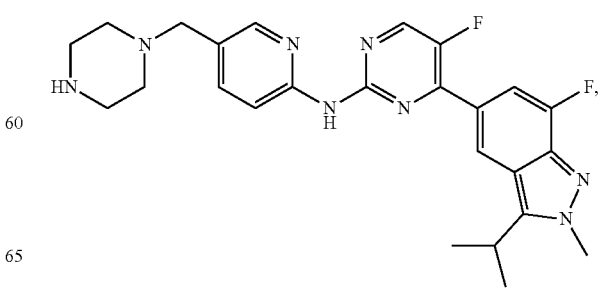

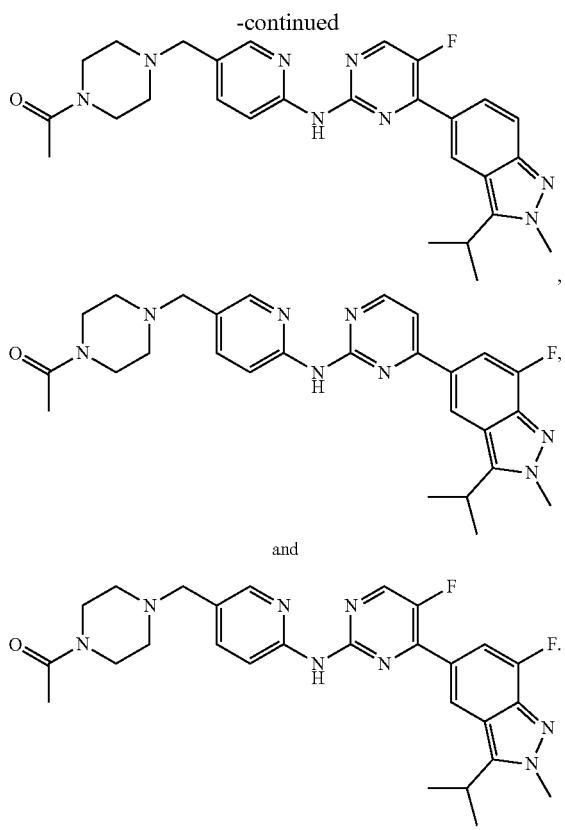

and

In another aspect, the present invention provides a pharmaceutical composition comprising a compound of formula (I), (Ia), (Ib), (Ic), (Id), or (Ie) according to any embodiments described here, or a pharmaceutically acceptable salt, solvate, or prodrug thereof, and one or more pharmaceutically acceptable adjuvants, diluents, and/or carriers.

In another aspect, the present invention provides a method of treating a disease, disorder, or condition mediated through activity of at least one cyclin-dependent kinase (CDK), comprising administering to a subject in need thereof a therapeutically effective amount of the compound of formula (I), (Ia), (Ib), (Ic), (Id), or (Ie) according to any of the embodiments described herein, or a pharmaceutically acceptable salt, solvate, or prodrug thereof.

In one embodiment of this aspect, the present invention provides a method of treating a disease, disorder, or condition mediated through activity of at least one cyclin-dependent kinase (CDK), comprising administering to a subject in need thereof a pharmaceutical composition comprising a therapeutically effective amount of the compound of formula (I), (Ia), (Ib), (Ic), (Id), or (Ie) according to any of the embodiments described herein, or a pharmaceutically acceptable salt, solvate, or prodrug thereof, and one or more pharmaceutically acceptable adjuvants, diluents, and/or carriers.

In one preferred embodiment of this aspect, the at least one CDK is CDK4, CDK6, or a combination thereof.

In another preferred embodiment of this aspect, the disease or disorder is a cancer or an inflammation-related disease or condition.

In another preferred embodiment of this aspect, the inflammation-related disease or condition is arthritis, such as rheumatic arthritis, or cystic fibrosis.

In another preferred embodiment of this aspect, the cancer is selected from, but not limited to, colorectal cancer, breast cancer, lung cancer, especially non-small cell lung cancer (NSCLC), prostate cancer, glioblastoma, mantel cell lymphoma (MCL), chronic myeloid leukemia (CML), acute myeloid leukemia (AML), and complications thereof.

In another embodiment of this aspect, the compound of the present invention may be administered to a subject in need thereof in combination with administration of a second therapeutic agent.

In another embodiment, the second therapeutic agent is a different CDK inhibitor, a human epidermal growth factor receptor (e.g., HER2) inhibitor, a serine/threonine kinase inhibitor, such as a mammalian target of rapamycin (mTOR) inhibitor, or an epidermal growth factor receptor (EGFR) inhibitor.

In another aspect, the present invention provides a method of inhibiting cell proliferation, comprising treating the cells with an effective amount of the compound of formula (I) according to any of the embodiments described, or a salt, solvate, prodrug, or composition thereof. The method of inhibiting cell proliferation can take place in vivo, e.g., inside the body of a subject, or in vitro, e.g., in a biological sample containing the proliferative cells of a subject.

In a preferred embodiment of this aspect, the proliferative cells are cancer cells, such as, but not limited to, cells of colorectal cancer, breast cancer, lung cancer, especially non-small cell lung cancer (NSCLC), prostate cancer, glioblastoma, mantel cell lymphoma (MCL), chronic myeloid leukemia (CML), acute myeloid leukemia (AML), or complications thereof.

In another aspect, the present invention provides a method of inhibiting a cyclin-dependent kinase (CDK) comprising treating said kinase with an effective amount of a compound of formula (I) according to any embodiments described herein, or a salt, solvate, prodrug, or composition thereof. The method of inhibiting CDK can take place in vivo, e.g., inside the body of a subject, or in vitro, e.g., in a biological sample containing the proliferative cells of a subject.

In a preferred embodiment of this aspect, the cyclin-dependent kinase is CDK4, CDK6, or a combination thereof.

In another aspect, the present invention provides use of a compound of formula (I), (Ia), (Ib), (Ic), (Id), or (Ie) according to any embodiments described herein, or a pharmaceutically acceptable salt, solvate, prodrug, or composition thereof, in the manufacture of a medicament for treatment of a disease or disorder associated with a CDK activity. The CDK activity is preferably activity of CDK4, CDK6, or a combination thereof.

In one embodiment of this aspect, the disease or disorder is selected from the group consisting of colorectal cancer, breast cancer, lung cancer, especially non-small cell lung cancer (NSCLC), prostate cancer, glioblastoma, mantel cell lymphoma (MCL), chronic myeloid leukemia (CML), and acute myeloid leukemia (AML).

In another embodiment of this aspect, the disease or disorder is an inflammation-related disease or condition, such as arthritis, in particular rheumatic arthritis, or cystic fibrosis.

In another aspect, the present invention provides a method of preparing compounds of formula (I), comprising a step of coupling intermediate E with intermediate G:

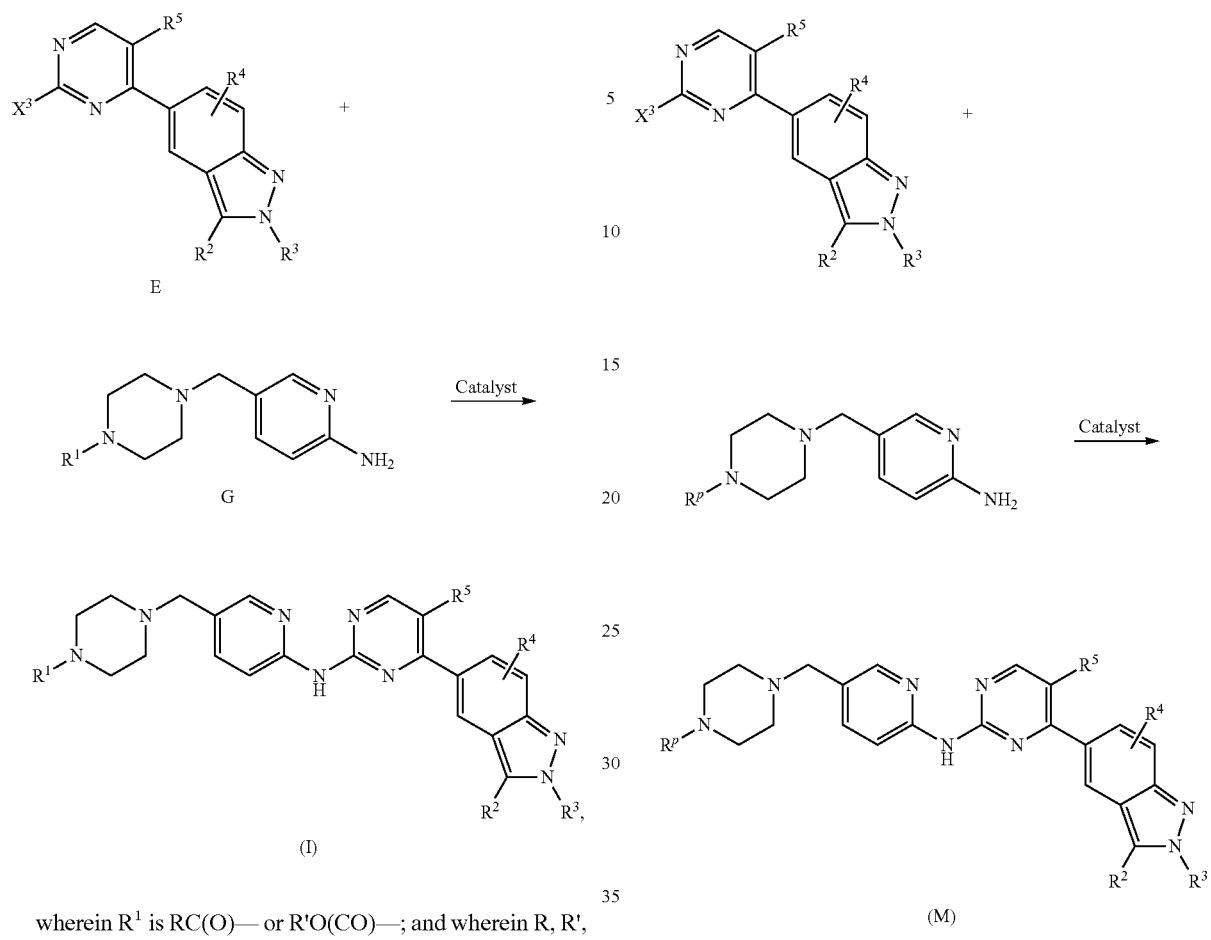

wherein $R^1$ is RC(O)— or R'O(CO)—; and wherein R, R', and $R^2$ through $R^5$ are defined according to any of the embodiments described herein, and $X^3$ is Cl, Br, or I.

When $R^1$ is hydrogen, it can be formed by base or acid catalyzed hydrolysis of the intermediate (M), where $R^p$ is a protecting group.

When $R^p$ is a protecting group, the method further comprises removal of $R^p$ through base and/or acid mediated hydrolysis (for example, removal of t-Boc group with HCl) to form the compound of formula (Iaa):

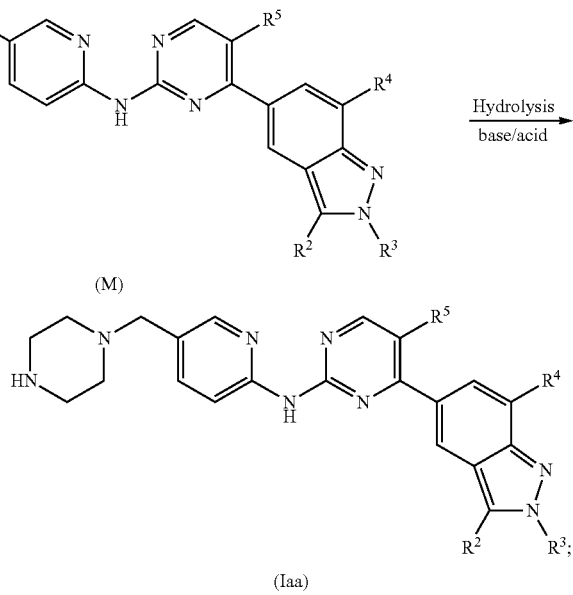

In a preferred embodiment, $R^p$ is t-BuOC(O)— ("t-Boc"), which can be readily removed by acid catalyzed hydrolysis to form the corresponding unsubstituted compound where $R^1$ is hydrogen.

The prodrugs disclosed herein can be optionally prepared through a reaction of the compound of formula (Iaa) with an acylating agent $R^1X^4$ to form $R^1$, wherein $R^1$ is RC(O)— or ROC(O)—, and $X^4$ is Cl or Br, or the corresponding anhydride $(RCO)_2O$.

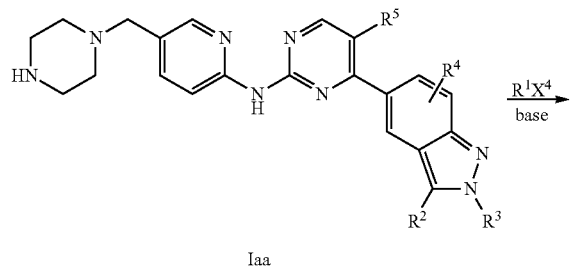

Iaa

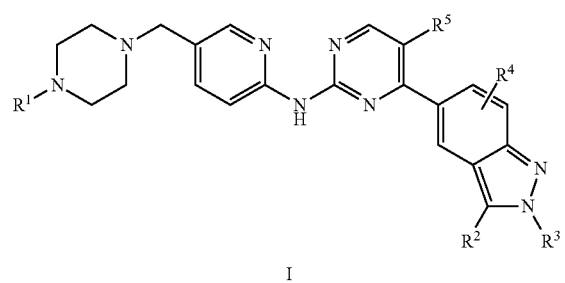

I

In one embodiment of this aspect, the method further includes the steps of converting intermediate C to intermediate D and coupling the intermediate D with a pyrimidine compound H to form the intermediate E:

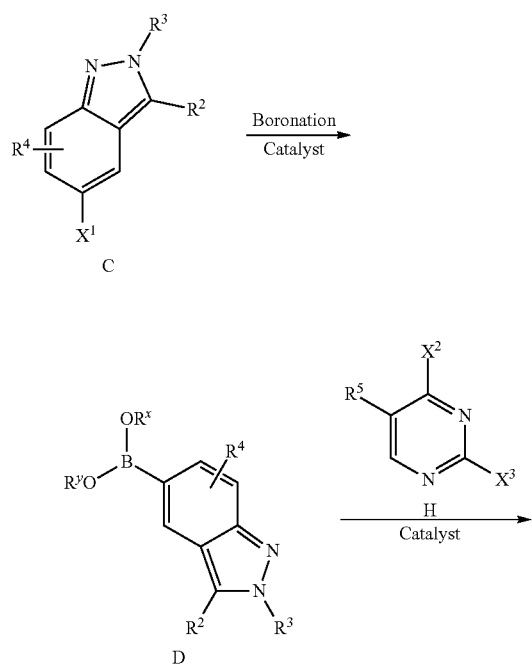

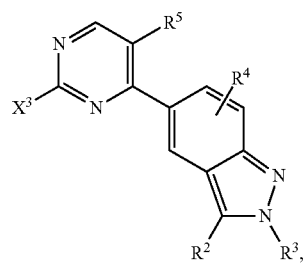

E wherein $R^x$ and $R^y$ are independent alkyl, aryl, cycloalkyl, or alternatively together form an alkylene group, each optionally substituted by one or more substituents independently selected from $C_1$-$C_4$ alkyl, halogen or phenyl; and wherein $X^1$, $X^2$, and $X^3$ are each independently Cl, Br, or I, on condition that the intermediate D couples with the compound H selectively at the $X^2$ site over the $X^3$ site, preferably having a higher than 90:10 selectivity, more preferably having a 95:5 selectivity, and most preferably exclusively at the $X^2$ site.

In one specific embodiment, boronation is realized through reaction of a bromide intermediate C (where $X^1$ is Br) with bis(pinacolato)diboron ($B_2pin_2$) in the presence of a catalyst, e.g., Pd(dppf)Cl$_2$, to form the 5-(pinacolato) boron-substituted 2H-indazole intermediate D, where $R^x$ and $R^y$ together form 1,1,2,2-tetramethyl-ethylene group. The intermediate D then reacts with compound 5-fluoro-2,4-dichloropyrimidine (H, where $R^5$ is fluoro, and both $X^2$ and $X^3$ are chloro) to form the desired 5-(pyrimidin-4-yl)-substituted 2H-indazole intermediate E ($R^5$ is F and $X^3$ is Cl).

In one embodiment of this aspect, the method further includes the steps of converting an ortho-nitrobenzaldehyde starting material S1 to intermediate A through phosphine-mediated condensation/cyclization and converting the intermediate A to the intermediate C through deprotonation and alkylation at the 3-position of the 2H-indazole intermediate A:

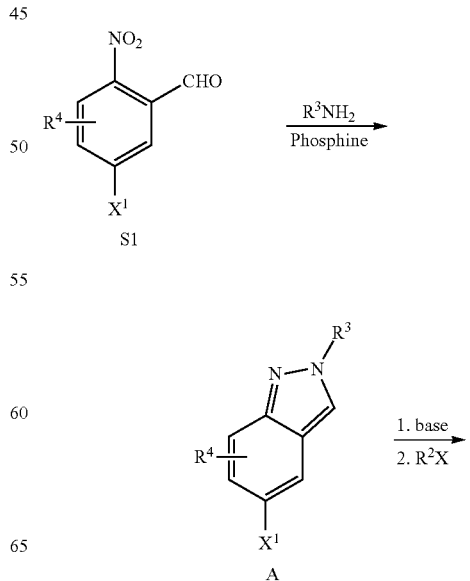

-continued

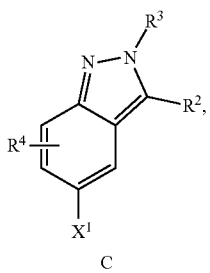

wherein $X^1$ is Cl, Br, I, or $MeSO_3$—; and wherein $R^2$ and $R^3$ are as defined according to any of the embodiments described herein.

In another embodiment of this aspect, alternatively, converting the intermediate A to the intermediate C comprises converting the intermediate A to an alcohol intermediate B followed by reduction of the alcohol intermediate B to form the intermediate C:

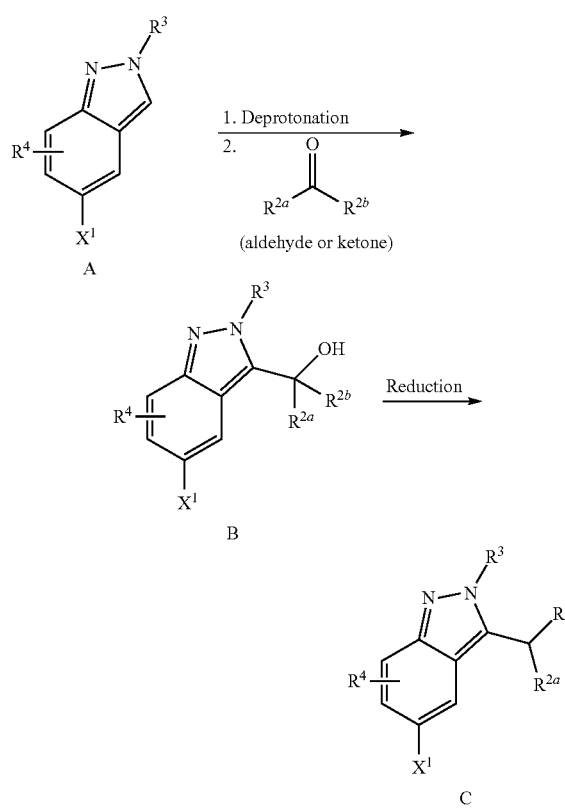

wherein $R^{2a}$ and $R^{2b}$ are each independently hydrogen, alkyl, cycloalkyl, or together form an alkylene group so that the group

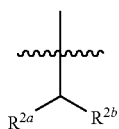

formed in the intermediate C is $R^2$ as defined according to any of the embodiments described herein. This approach is particularly convenient for preparation of intermediate C where $R^2$ is ethyl, propyl, isopropyl, iso-butyl, cycloalkyl, cycloalkylmethyl, or the like, by using the corresponding aldehyde or ketone as the alkylating agent or solvent.

In one embodiment of this aspect, the method further includes a step of forming the intermediate G through coupling the pyridine aldehyde compound S2 and the piperazine compound S3 to form an intermediate F, followed by converting the intermediate F to the intermediate G:

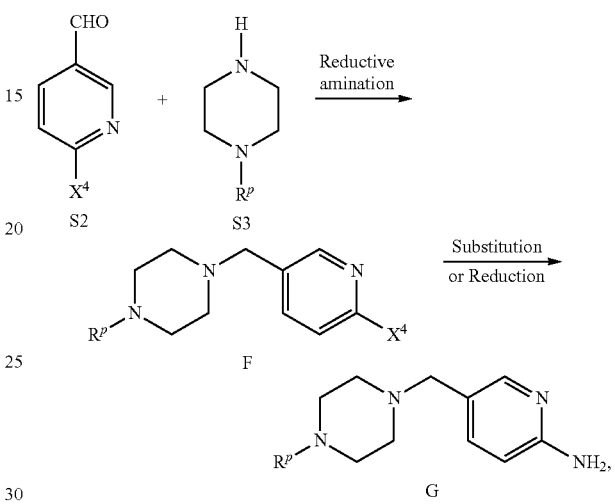

wherein $R^p$ is a protecting group or $R^1$, where $R^1$ is RC(O)— or ROC(O)—; $X^4$ is selected from the group consisting of Cl, Br, I, and —$NO_2$; and wherein said converting the intermediate F to the intermediate G comprises replacing $X^4$ with $NH_2$ when $X^4$ is Cl, Br, or I; or alternatively reducing the nitro group (—$NO_2$) to amino group (—$NH_2$) when $X^4$ is —$NO_2$.

Compounds provided by this invention are also useful for the study of kinases in biological and pathological phenomena, the study of transduction pathways mediated by such kinases, and the comparative evaluation of new kinase inhibitors.

Unless otherwise indicated, the term "alkyl," as used herein, is intended to include both branched and straight-chain saturated aliphatic hydrocarbon groups containing 1 to 8 carbons, preferably 1 to 6, more preferably 1 to 4, carbons. The term encompasses, but is not limited to, methyl, ethyl, propyl, isopropyl, butyl, t-butyl, isobutyl, pentyl, hexyl, or the like.

Unless otherwise indicated, the term "alkylene," as used herein, refers to a bivalent saturated aliphatic radical derived from an alkane by removal of two hydrogen atoms. Examples include, but are not limited to, methylene (—$CH_2$—), ethylene (—$CH_2CH_2$—), propylene (—$CH_2CH_2CH_2$—), or the like.

Unless otherwise indicated, the term "cycloalkyl", as used herein alone or as a part of another group, includes saturated cyclic hydrocarbon radical having 3 to 8 carbons forming the ring. Examples include, but are not limited to, cyclopropyl, cyclobutyl, cyclopentyl, and cyclohexyl.

Unless otherwise indicated, the term "aryl", as used herein alone or as part of another group, refers to monocyclic or bicyclic aromatic radical containing 6 to 10 carbons in the ring portion (such as phenyl and naphthyl, including 1-naphthyl and 2-naphthyl).

"Halo" or "halogen" as used herein, refers to fluoro (F), chloro (Cl), bromo (Br), and iodo (I).

Further, the alkyl, alkylene, cycloalkyl, and cycloalkylmethyl groups optionally can be independently further substituted with one or more, preferably 1 to 3, substituents independently selected from the group consisting of halogen and $C_1$-$C_4$ alkyl.

The compounds of the present invention are generally recognized as organic bases, which are able to react with acids, specifically pharmaceutically acceptable acids, to form pharmaceutically acceptable salts.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. See, e.g., S. M. Berge et al., J. Pharm. Sci., 1977, 66, 1-19, which is incorporated herein by reference. Pharmaceutically acceptable salts of the compounds of this invention include those derived from suitable inorganic and organic acids. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Preferred pharmaceutically acceptable salts include the hydrochloride salts.

The term "solvate," as used herein, means a physical association of a compound of this invention with a stoichiometric or non-stoichiometric amount of solvent molecules. For example, one molecule of the compound associates with one or more, preferably one to three, solvent molecules. It is also possible that multiple (e.g., 1.5 or 2) molecules of the compound share one solvent molecule. This physical association may include hydrogen bonding. In certain instances the solvates will be capable of isolation as crystalline solid. The solvent molecules in the solvate may be present in a regular arrangement and/or a non-ordered arrangement. Exemplary solvates include, but are not limited to, hydrates, ethanolates, methanolates, and isopropanolates. Methods of solvation are generally known in the art.

Although the compounds of general formula (I) disclosed herein may be in the "prodrug" forms themselves, i.e., when $R^1$ is an acyl (i.e., RC(O)—) or ester (i.e., ROC(O)—) group, these "prodrugs" may be generated in vivo under physiological conditions from other "prodrugs". Thus, for these compounds disclosed, the term "prodrug," as used herein, refers to a derivative of a compound that can be transformed in vivo to yield the parent compound, for example, by hydrolysis in blood. Common examples of prodrugs in the present invention include, but are not limited to, amide or phosphoramide forms of an active amine compound, for example, the compound of formula (II):

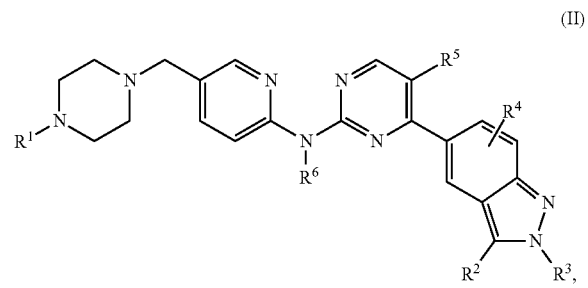

(II)

wherein $R^6$ is an acyl group (e.g., acetyl, propionyl, formyl, etc.) or phosphoryl [e.g., —P(=O)(OH)$_2$] group; or alternatively, when $R^3$ in an active compound is hydrogen, the corresponding amide or phosphoramide compounds may serve as prodrugs. Such amide or phosphoramide prodrug compounds may be prepared according to conventional methods as known in the art.

When it is possible that, for use in therapy, therapeutically effective amounts of a compound of the present invention, or pharmaceutically acceptable salts or solvates thereof, may be administered as the raw chemical, it is possible to present the active ingredient as a pharmaceutical composition. Accordingly, the disclosure further provides pharmaceutical compositions, which include any compounds of the present invention, or pharmaceutically acceptable salts or solvates thereof, and one or more, preferably one to three, pharmaceutically acceptable carriers, diluents, or other excipients. The carrier(s), diluent(s), or other excipient(s) must be acceptable in the sense of being compatible with the other ingredients of the formulation and not deleterious to the subject being treated.

The term "pharmaceutically acceptable," as used herein, refers to the property of those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Typically, the pharmaceutical compositions of this disclosure will be administered from once every 1 to 5 days to about 1-5 times per day, or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford effective results without causing substantial harmful or deleterious side effects.

When the compositions of this disclosure comprise a combination of a compound of the present disclosure and one or more, preferably one or two, additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example, by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an alginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release, for example, by coating or embedding particulate material in polymers, wax, or the like.

It should be understood that in addition to the ingredients particularly mentioned above, the formulations may include other agents conventional in the art having regard to the type of formulation in question, for example those suitable for oral administration may include flavoring agents.

The term "subject" or "patient" includes both humans and other mammalian animals, preferably humans.

The term "therapeutically effective amount" refers to an amount of a compound or composition that, when administered to a subject for treating a disease, is sufficient to effect such treatment for the disease. A "therapeutically effective amount" can vary depending on, inter alia, the compound, the disease and its severity, and the age, weight, or other factors of the subject to be treated. When applied to an individual active ingredient, administered alone, the term refers to that ingredient alone. When applied to a combination, the term refers to combined amounts of the active ingredients that result in the therapeutic effect, whether administered in combination, serially, or simultaneously.

In some embodiments, the term "treating" or "treatment" refers to inhibiting the disease, disorder, or condition, i.e., arresting its development; or relieving the disease, disorder, or condition, i.e., causing regression of the disease, disorder, and/or condition. Thus, in some embodiments, "treating" or "treatment" refers to ameliorating a disease or disorder, which may include ameliorating one or more physical parameters, though maybe indiscernible by the subject being treated. In some embodiments, "treating" or "treatment" includes modulating the disease or disorder, either physically (e.g., stabilization of a discernible symptom) or physiologically (e.g., stabilization of a physical parameter) or both. In yet some embodiments, "treating" or "treatment" includes delaying the onset of the disease or disorder.

Methods

Abbreviations

The following abbreviations may be used in this application:

B₂pin₂=bis(pinacolato)diboron
MeOH=methanol
LDA=lithium diisopropylamide
LiHMDS=lithium bis(trimethylsilyl)amide [LiN(SiMe₃)₂]
Pd(dppf)Cl₂=[1,1'-bis(diphenylphosphino)ferrocene]dichloropalladium(II)
Pd₂(dba)₃=tris(dibenzylideneacetone)dipalladium(0)
Xantphos=4,5-bis(diphenylphosphino)-9,9-dimethylxanthene
nBu₃P=tri-n-butylphosphine
DCM=dichloromethane
THF=tetrahydrofuran;
DIEA=DIPEA=diisopropylethylamine;
sat.=saturated aqueous solution;
aq.=aqueous
FCC=flash column chromatography using silica;
TFA=trifluoroacetic acid;
r.t.=room temperature;
DMF=N,N-dimethylformamide;
DMSO=dimethylsulfoxide;
DMA=N,N-dimethylacetamide;
EtOAc=ethyl acetate;
h=hour(s).

Chemical Synthesis

Synthesis of Compounds of Formula (I)

The synthesis of compounds of formula (I) is exemplified in the General Synthetic Schemes 1-4:

1. Synthesis of the Indazole Intermediate C (Scheme 1)

A suitable 5-halo-2-nitrobenzaldehyde starting material S1 ($X^1$=Cl, Br, or I) is allowed to react with a primary amine ($R^3NH_2$) in the presence of a phosphine, e.g., tri-butylphosphine, to form the indazole derivative A (Genung, N. E. et al. *Org. Lett.* 2014 16, 3114-3117), which in turn is deprotonated at the 3-position using a strong base, e.g., LDA, followed by reaction with an alkylation reagent $R^2X$ (X=e.g., Cl, Br, I, or methanesulfonate) to form the intermediate C with the desired $R^2$, $R^3$, and $R^4$ in place. Alternatively, the deprotonated compound A can be allowed to react with an aldehyde or ketone to form an alcohol adduct, which is reduced (e.g., by a dialkylsilane) to form the desired intermediate C.

Scheme 1

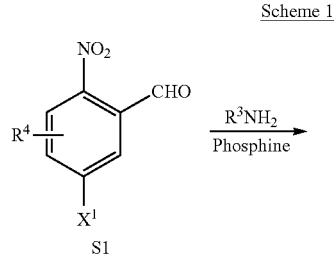

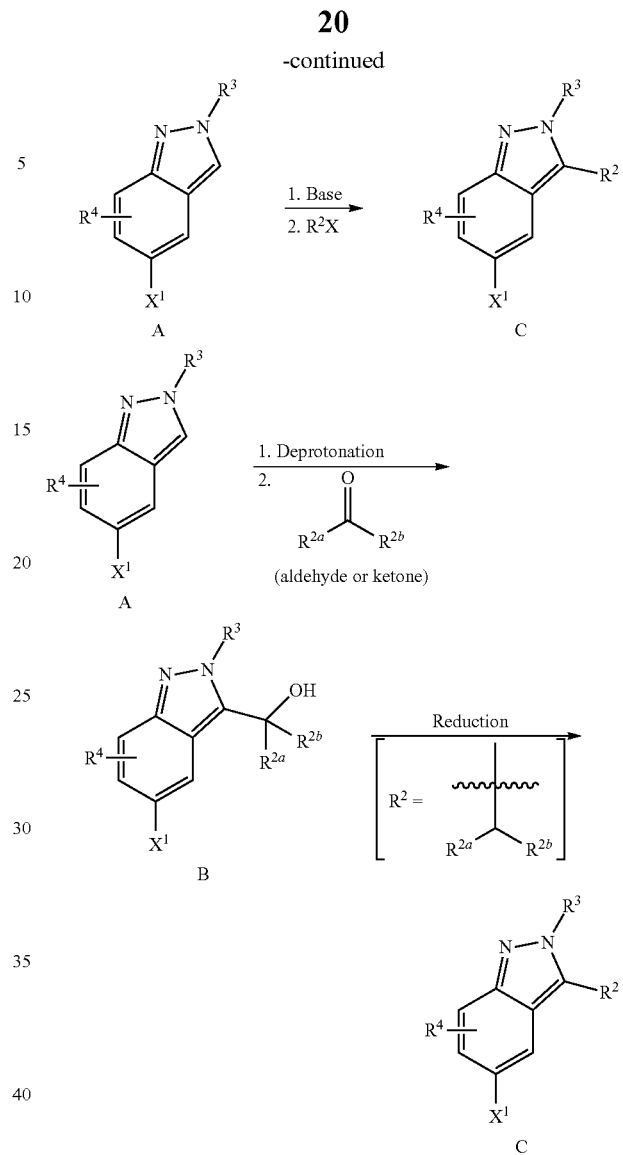

2. Synthesis of the Pyrimidine-Substituted 2H-Indazole Intermediate E (Scheme 2)

The intermediate C is allowed to undergo a boronation reaction in the presence of a catalyst (e.g., a palladium catalyst) to form the boronate intermediate D, which is allowed to couple with a halogen-substituted pyrimidine derivative H to form a 5-(pyrimidin-3-yl)-indazole intermediate E.

Scheme 2

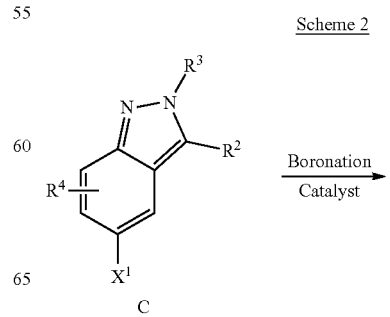

21
-continued

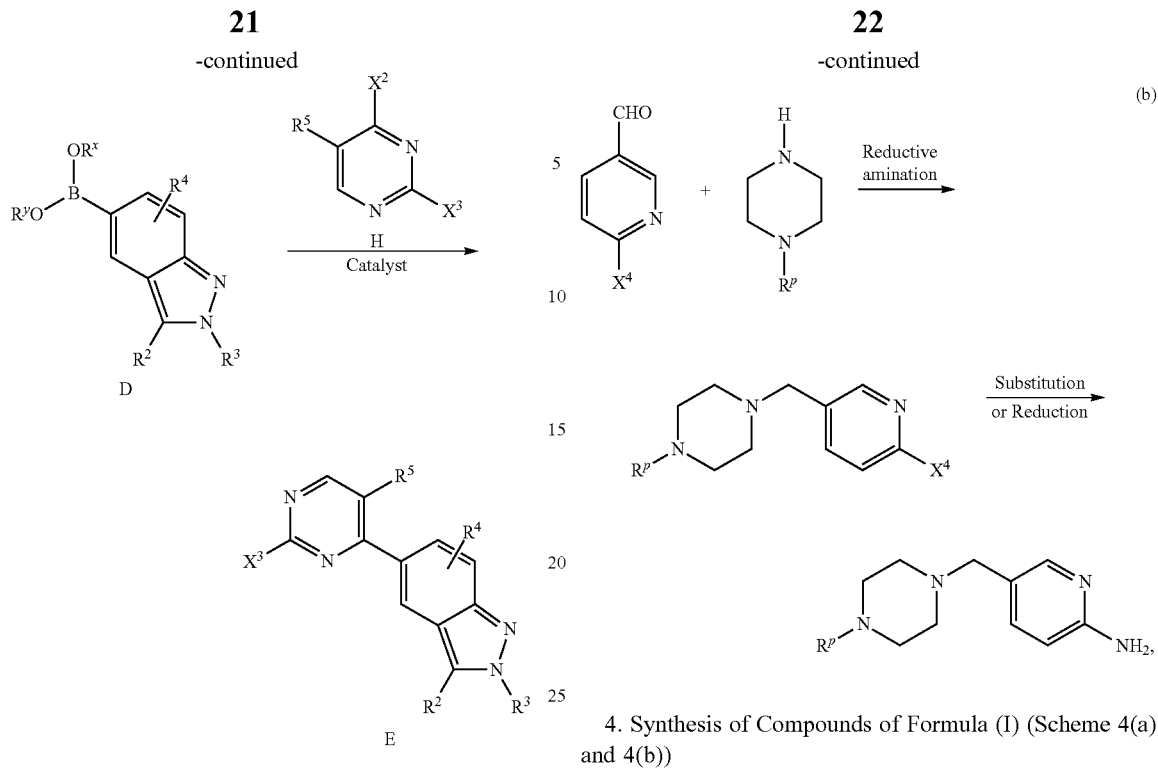

3. Synthesis of the 2-amino-5-piperazinylmethyl-pyridine Intermediate G (Scheme 3(a) and 3(b))

A 6-halogen or 6-nitro substituted pyridine-3-carbaldehyde starting material S2 and a 1-R$^1$-substituted (where R$^1$ is not hydrogen) or 1-R$^p$-substituted piperazine starting material S3 are allowed to undergo a reductive amination reaction to form a 2-amino-5-piperazinylmethyl-pyridine intermediate F, which is in turn converted to the 2-amino-5-piperazinylmethyl-pyridine intermediate G through substitution of the halogen or reduction of nitro group on the pyridine ring.

Scheme 3

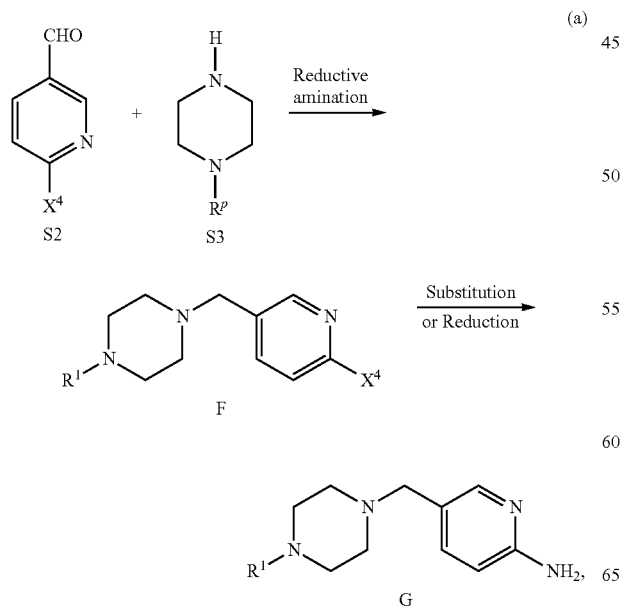

22
-continued (b)

4. Synthesis of Compounds of Formula (I) (Scheme 4(a) and 4(b))

Coupling of the pyrimidine-substituted 2H-indazole intermediate E with the 2-amino-5-piperazinemethyl-pyridine intermediate G in the presence of a catalyst (e.g., palladium catalyst) provides the compound of formula (I), where R$^1$ is not hydrogen. Alternatively, coupling of the 2H-indazole intermediate E with an R$^p$-substituted intermediate G forms an intermediate (M), followed by removal of the protecting group R$^p$ to form the compound of formula (I), where R$^1$ is hydrogen. The latter can also be further converted to other compounds of formula (I), wherein R$^1$ is not hydrogen, by reacting with an acylating agent.

Scheme 4

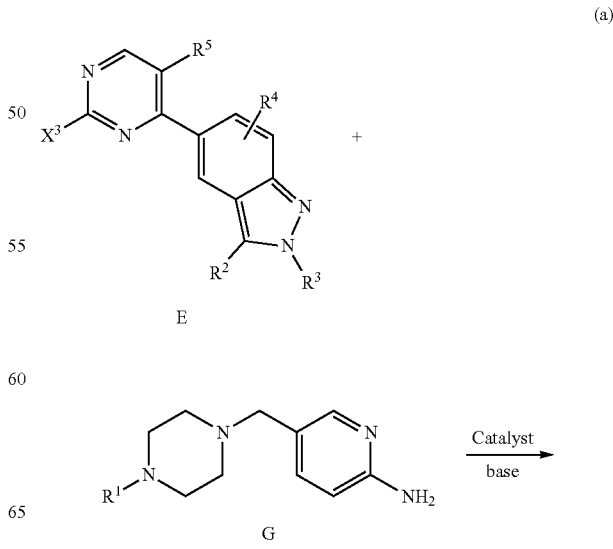

-continued

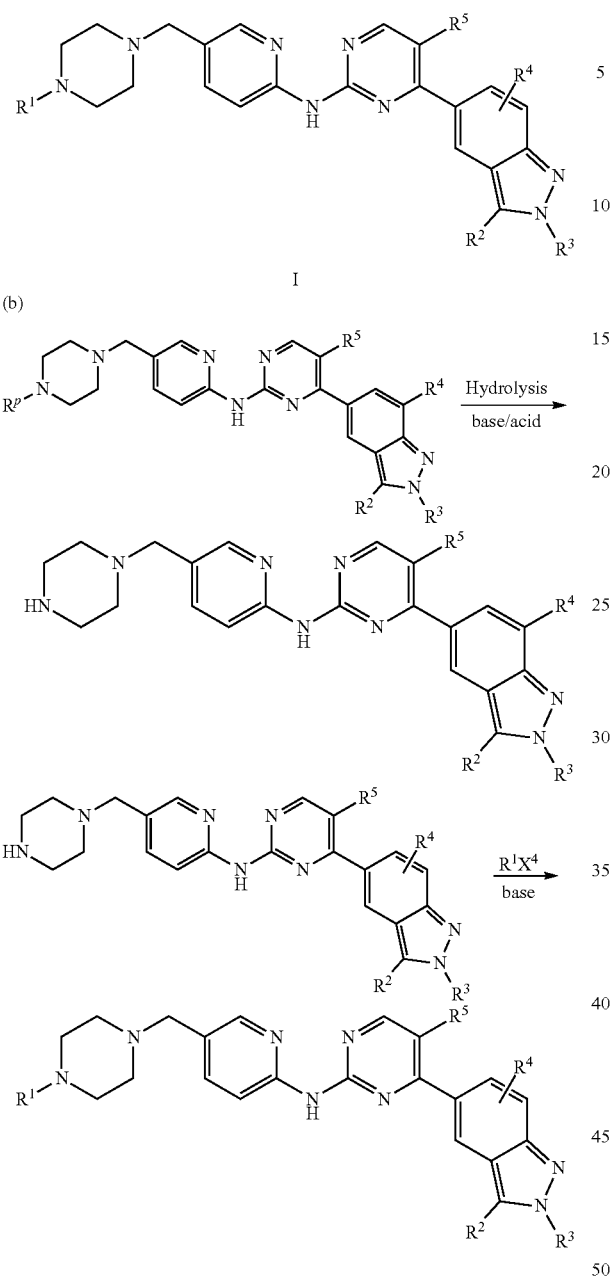

Examples

The following non-limiting Examples further illustrate certain aspects of the present invention. These compounds are prepared according to the general Synthetic Schemes described above.

5-Fluoro-4-(3-isopropyl-2-methyl-2H-indazol-5-yl)-N-(5-(piperazin-1-methyl)pyridin-2-yl)pyrimidin-2-amine hydrochloride (1.HCl)

Compound 1 was prepared using Scheme 5 below, and the experimental details are further described for illustration purpose.

Scheme 5

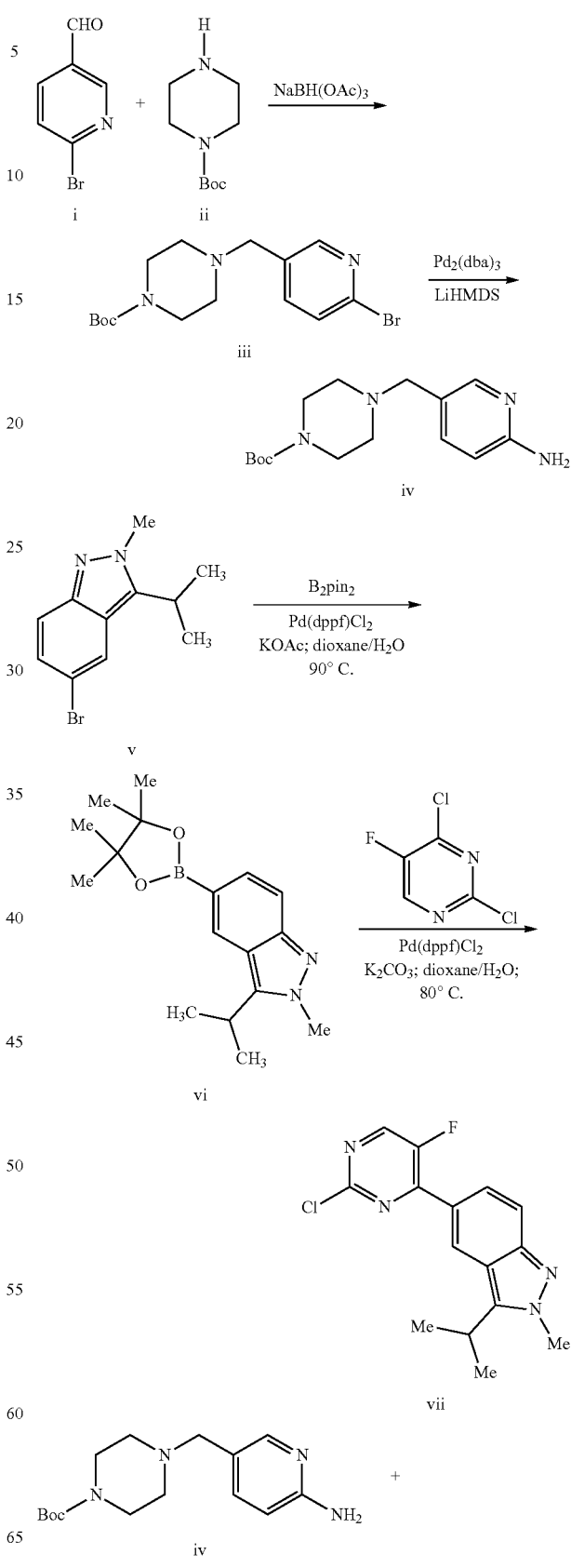

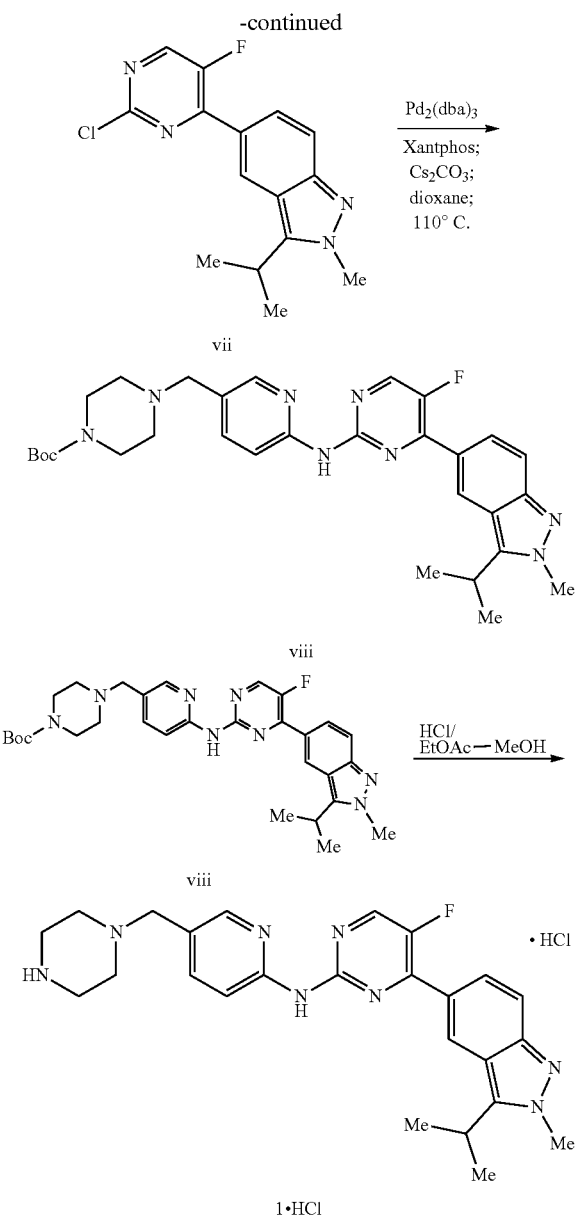

t-Butyl 4-((6-bromopyridin-3-yl)methyl)piperazine-1-carboxylate (iii)

A solution of 5-bromopyridine-2-carbaldehyde (i; 71.4 g, 384 mmol, 1 equiv), 1-Boc-piperazine (ii; 72.8 g, 391 mmol, 1.02 equiv), dichloromethane (1.2 L), and acetic acid (2.4 mL) was cooled to 15° C. and sodium triacetoxyborohydride (164.9 g, 777.8 mmol, 2.03 equiv) was added portionwise to the mixture at 25° C. The resulting solution was stirred for 24 h at room temperature. An additional portion of sodium triacetoxyborohydride (13 g, 61.3 mmol, 0.16 equiv) was added portionwise at 15° C. The reaction was then quenched with aq 2N NaOH (250 mL) and the resulting solution was stirred for another 0.5 h. The organic layer was washed twice with water, dried and concentrated. The residue was recrystallized with 4:1 petroleum ether/ethyl acetate to yield 107.7 g (78% yield) of iii as a light yellow solid.

t-Butyl 4-((6-aminopyridin-3-yl)methyl)piperazine-1-carboxylate (iv)

A solution of intermediate iii (100 g, 281 mmol, 1 equiv), $Cu_2O$ (20 g 140 mmol, 0.5 equiv), and aq $NH_3 \cdot H_2O$ (250 mL, 2.5 equiv) was stirred for 8 h at 120° C. (16 Mpa) in a 500 mL autoclave. The solution was cooled to room temperature then quenched with aq 2N NaOH solution (1 L) and extracted twice with $CH_2Cl_2$. The organic phase was washed with 15 L of brine, then dried and concentrated. Purification by column chromatography (50:1 to 10:1 $CH_2C_2$/MeOH on silica gel) resulted in 25.4 g (31% yield) of iv as an off-white solid.

5-(2-Chloro-5-fluoropyrimidin-4-yl)-3-isopropyl-2-methyl-2H-indazole (vii)

A solution of 5-bromo-3-isopropyl-2-methyl-2H-indazole (v; 30 g, 118 mmol, 1 equiv), 4,4,5,5-tetramethyl-2-(tetramethyl-1,3,2-dioxaborolan-2-yl)-1,3,2-dioxaborolane (36.1 g, 142 mmol, 1.2 equiv), KOAc (23.3 g, 237.8 mmol, 2 equiv), in DMF (150 mL) was degassed. $Pd(dppf)Cl_2$ (2.6 g, 0.01 equiv) was added and the reaction mixture was stirred under a $N_2$ atmosphere for 8 h at 90-100° C., cooled to 30-40° C. and then diluted with 300 mL of water. The mixture was stirred for 1-2 h at 0-10° C. and the product was collected by filtration. The filter cake was washed with water to afford 3-isopropyl-2-methyl-5-(4,4,5,5-tetramethyl-1,3,2-dioxaborolan-2-yl)-2H-indazole (vi). which was used directly in the next step.

A degassed mixture of intermediate vi (1 equiv), 2,4-dichloro-5-fluoropyrimidine (23.75 g, 180 mmol, 1.2 equiv), $K_2CO_3$ (32.76 g, 237 mmol, 1.3 equiv), $Pd(dppf)Cl_2$ (0.87 g, 0.03 equiv), 1,4-dioxane (300 mL), and water (60 mL, 2 equiv) was stirred for 5-8 h at 85-95° C. under a $N_2$ atmosphere. After cooling to 30-40° C., the reaction mixture was filtered and the filtrate was partially concentrated in vacuo and then added slowly to 300 mL of water. The resulting mixture was extracted with dichloromethane and the organic phase was washed with water, dried, concentrated and purified by column chromatography (50:1 to 10:1 $CH_2Cl_2$/MeOH on silica gel) to yield 14.8 g (40% yield) of vii as of an off white solid. $^1$H NMR (300 MHz, $CDCl_3$, $\delta$): 1.58 (d, 6H), 3.48-3.57 (m, 1H), 4.19 (s, 3H), 7.24 (d, 1H), 8.03-8.07 (m, 1H), 8.47 (d, 1H), 8.68 (s, 1H); LC-MS (ES+) m/z: 305 (M+H)$^+$.

t-Butyl-4-((6-((5-fluoro-4-(3-isopropyl-2-methyl-2H-indazol-5-yl)pyrimidin-2-yl)amino)pyridin-3-yl)methyl)piperazine-1-carboxylate (viii)

A mixture of vii (14.8 g, 484 mmol, 1.0 equiv), iv (16.3 g, 557 mmol, 1.15 equiv), $K_3PO_4 \cdot 3H_2O$ (25.8 g, 967 mmol, 2.0 equiv), $Pd(dba)_3$ (1.3 g, 1.5 mmol, 0.03 equiv) and Xantphos (0.8 g, 1.5 mmol, 0.03 equiv) in 150 mL of 1,4-dioxane was degassed with $N_2$, then heated while stirring at 90-100° C. for 24 h. Additional $Pd(dba)_3$ (0.42 g, 0.72 mmol, 0.015 equiv) and Xantphos (0.42 g, 0.72 mmol, 0.015 equiv) were added and heating at 90-100° C. with stirring was continued for 8 h. The reaction mixture was cooled to 40-50° C., added to ice-water (300 mL), stirred for 3-5 h and extracted with dichloromethane. The organic phase was washed with water, dried and concentrated in vacuo. Purification by column chromatography (50:1 to 10:1 $CH_2Cl_2$/MeOH on silica gel) provided 22.8 g (84% yield) of viii as an off-white solid.

5-Fluoro-4-(3-isopropyl-2-methyl-2H-indazol-5-yl)-N-(5-(piperazin-1-ylmethyl)pyridin-2-yl)pyrimidin-2-amine hydrochloride (1.HCl)

A solution of viii (25.1 g, 604 mmol, 1.0 equiv) in a mixture of HCl (g) in ethyl acetate/methanol (500 mL) was stirred at room temperature for 24 h. The solution was concentrated to yield 29.8 g (99% yield) of 1.HCl as an off-white solid. $^1$HNMR (300 MHz, D$_2$O, δ): 1.44 (d, 6H, J=7 Hz), 3.44-3.56 (overlapping m, 9H), 4.06 (s, 3H), 4.32 (s, 2H), 7.43 (d, 1H, J=7.4), 7.55 (d, 1H, J=7.6), 8.00-8.63 (m, 5H) ppm; LC-MS (ES+) m/z: 461 (M+H)$^+$.

The free base form of 1 can be formed by standard techniques that employ appropriate bases such as NaOH, Na$_2$CO$_3$, etc.

Compounds 1 and other selected examples (Compounds 2-36) of the present invention are listed in Table 1, all of which are or can be prepared according to the methods described herein.

TABLE 1

Selected examples of the compounds of formula (I)

| Example | Structure | Name |
| --- | --- | --- |
| 1 | 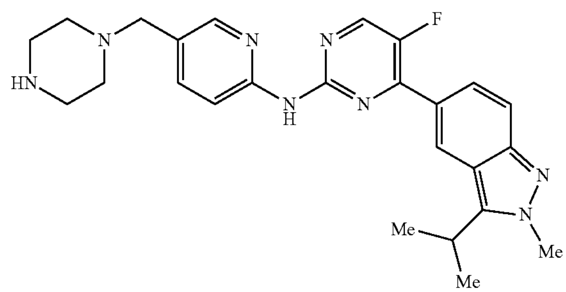 [SMILES: CC(C)c1c2cc(-c3nc(Nc4ccc(CN5CCNCC5)cn4)ncc3F)ccc2nn1C] | 5-fluoro-4-(3-isopropyl-2-methyl-2H-indazol-5-yl)-N-(5-(piperazin-1-ylmethyl)pyridin-2-yl)pyrimidin-2-amine |
| 2 | 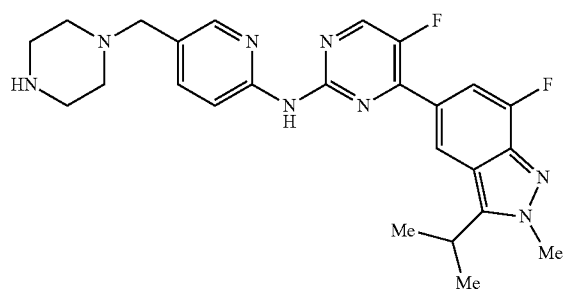 [SMILES: CC(C)c1c2cc(-c3nc(Nc4ccc(CN5CCNCC5)cn4)ncc3F)cc(F)c2nn1C] | 5-fluoro-4-(7-fluoro-3-isopropyl-2-methyl-2H-indazol-5-yl)-N-(5-(piperazin-1-ylmethyl)pyridin-2-yl)pyrimidin-2-amine |
| 3 | 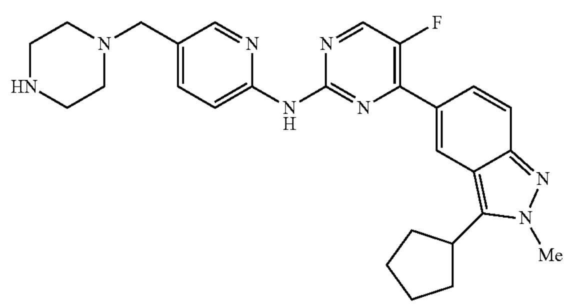 [SMILES: Cn1nc2ccc(-c3nc(Nc4ccc(CN5CCNCC5)cn4)ncc3F)cc2c1C1CCCC1] | 4-(3-cyclopentyl-2-methyl-2H-indazol-5-yl)-5-fluoro-N-(5-(piperazin-1-ylmethyl)pyridin-2-yl)pyrimidin-2-amine |
| 4 | 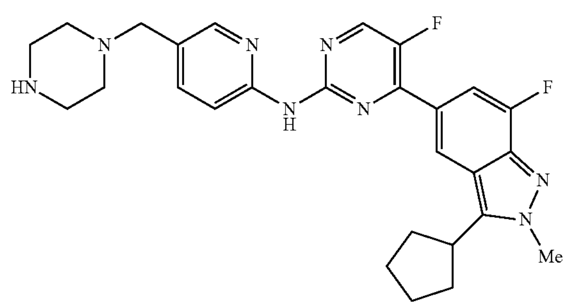 [SMILES: Cn1nc2c(F)cc(-c3nc(Nc4ccc(CN5CCNCC5)cn4)ncc3F)cc2c1C1CCCC1] | 4-(3-cyclopentyl-7-fluoro-2-methyl-2H-indazol-5-yl)-5-fluoro-N-(5-(piperazin-1-ylmethyl)pyridin-2-yl)pyrimidin-2-amine |

TABLE 1-continued

Selected examples of the compounds of formula (I)

| Example | Structure | Name |
|---|---|---|
| 5 | 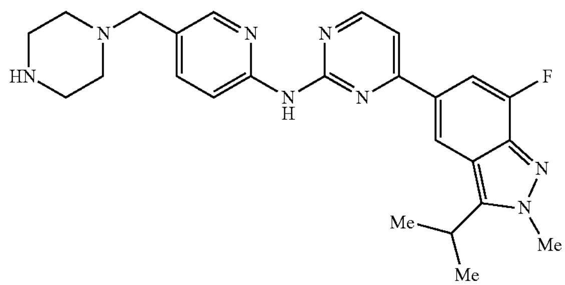 [SMILES: CC(C)c1c2cc(-c3ccnc(Nc4ccc(CN5CCNCC5)cn4)n3)cc(F)c2nn1C] | 4-(7-fluoro-3-isopropyl-2-methyl-2H-indazol-5-yl)-N-(5-(piperazin-1-ylmethyl)pyridin-2-yl)pyrimidin-2-amine |
| 6 | 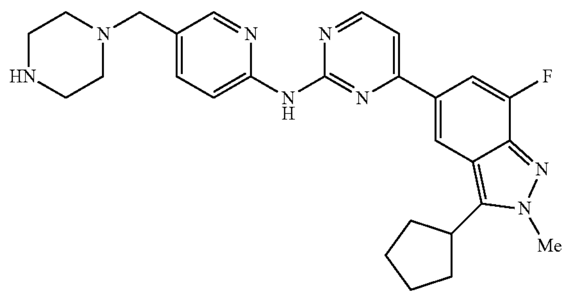 [SMILES: Cn1nc2c(F)cc(-c3ccnc(Nc4ccc(CN5CCNCC5)cn4)n3)cc2c1C1CCCC1] | 4-(3-cyclopentyl-7-fluoro-2-methyl-2H-indazol-5-yl)-N-(5-(piperazin-1-ylmethyl)pyridin-2-yl)pyrimidin-2-amine |
| 7 | 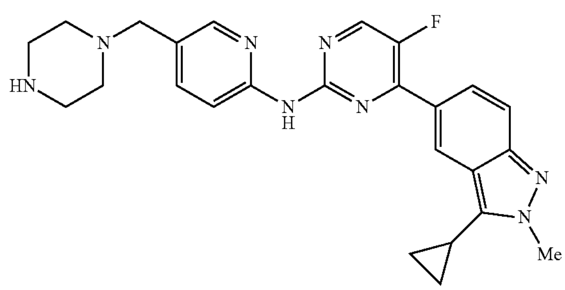 [SMILES: Cn1nc2ccc(-c3nc(Nc4ccc(CN5CCNCC5)cn4)ncc3F)cc2c1C1CC1] | 4-(3-cyclopropyl-2-methyl-2H-indazol-5-yl)-5-fluoro-N-(5-(piperazin-1-ylmethyl)pyridin-2-yl)pyrimidin-2-amine |
| 8 | 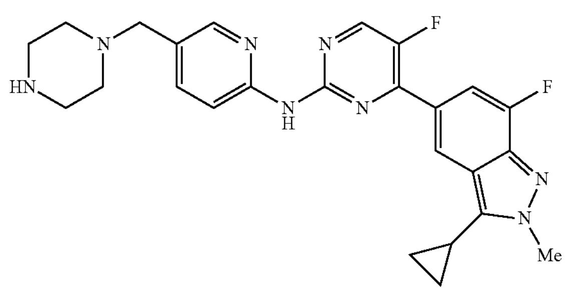 [SMILES: Cn1nc2c(F)cc(-c3nc(Nc4ccc(CN5CCNCC5)cn4)ncc3F)cc2c1C1CC1] | 4-(3-cyclopropyl-7-fluoro-2-methyl-2H-indazol-5-yl)-5-fluoro-N-(5-(piperazin-1-ylmethyl)pyridin-2-yl)pyrimidin-2-amine |
| 9 | 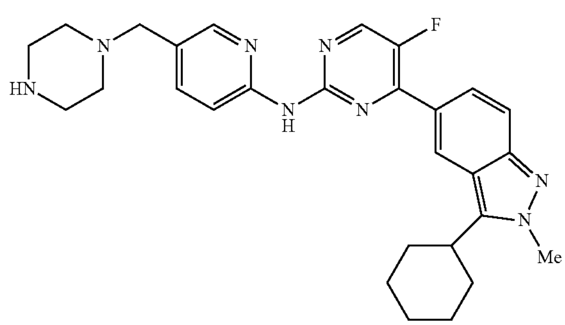 [SMILES: Cn1nc2ccc(-c3nc(Nc4ccc(CN5CCNCC5)cn4)ncc3F)cc2c1C1CCCCC1] | 4-(3-cyclohexyl-2-methyl-2H-indazol-5-yl)-5-fluoro-N-(5-(piperazin-1-ylmethyl)pyridin-2-yl)pyrimidin-2-amine |

TABLE 1-continued

Selected examples of the compounds of formula (I)

| Example | Structure | Name |
|---|---|---|
| 10 | 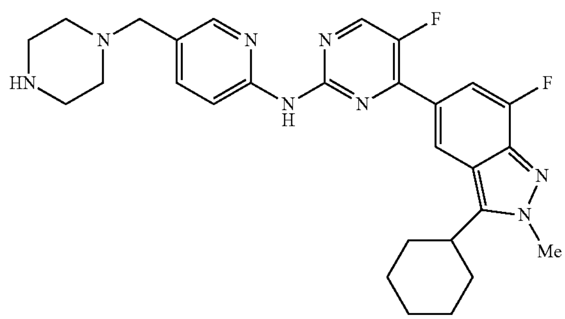 [SMILES: Cn1nc2c(F)cc(-c3nc(Nc4ccc(CN5CCNCC5)cn4)ncc3F)cc2c1C1CCCCC1] | 4-(3-cyclohexyl-7-fluoro-2-methyl-2H-indazol-5-yl)-5-fluoro-N-(5-(piperazin-1-ylmethyl)pyridin-2-yl)pyrimidin-2-amine |
| 11 | 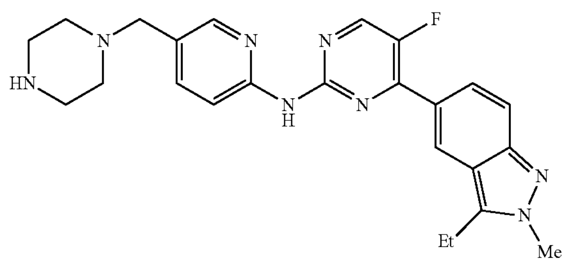 [SMILES: CCc1c2cc(-c3nc(Nc4ccc(CN5CCNCC5)cn4)ncc3F)ccc2nn1C] | 4-(3-ethyl-2-methyl-2H-indazol-5-yl)-5-fluoro-N-(5-(piperazin-1-ylmethyl)pyridin-2-yl)pyrimidin-2-amine |
| 12 | 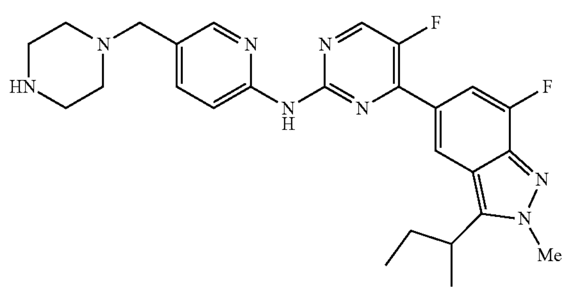 [SMILES: CCC(C)c1c2cc(-c3nc(Nc4ccc(CN5CCNCC5)cn4)ncc3F)cc(F)c2nn1C] | 4-(3-(sec-butyl)-7-fluoro-2-methyl-2H-indazol-5-yl)-5-fluoro-N-(5-(piperazin-1-ylmethyl)pyridin-2-yl)pyrimidin-2-amine |
| 13 | 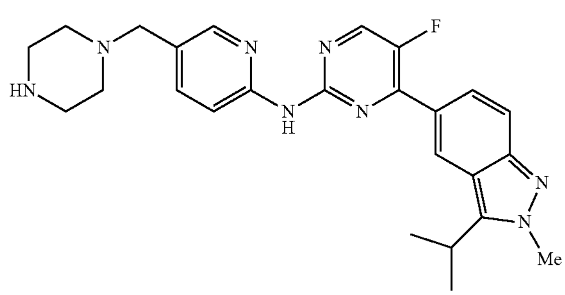 [SMILES: CC(C)c1c2cc(-c3nc(Nc4ccc(CN5CCNCC5)cn4)ncc3F)ccc2nn1C] | 4-(2-ethyl-3-isopropyl-2H-indazol-5-yl)-5-fluoro-N-(5-(piperazin-1-ylmethyl)pyridin-2-yl)pyrimidin-2-amine |
| 14 | 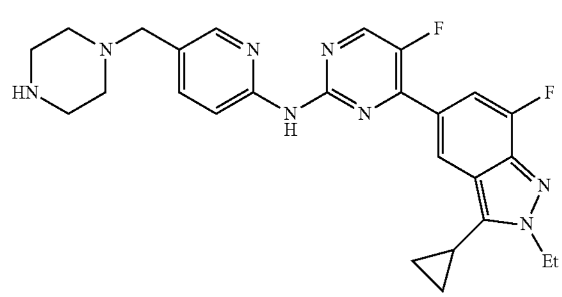 [SMILES: CCn1nc2c(F)cc(-c3nc(Nc4ccc(CN5CCNCC5)cn4)ncc3F)cc2c1C1CC1] | 4-(3-cyclopropyl-2-ethyl-7-fluoro-2H-indazol-5-yl)-5-fluoro-N-(5-(piperazin-1-ylmethyl)pyridin-2-yl)pyrimidin-2-amine |

TABLE 1-continued

Selected examples of the compounds of formula (I)

| Example | Structure | Name |
|---|---|---|
| 15 | 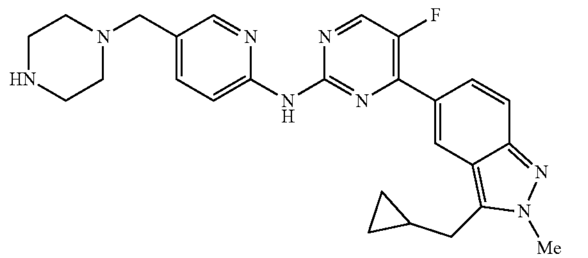 [SMILES: Cn1nc2ccc(-c3nc(Nc4ccc(CN5CCNCC5)cn4)ncc3F)cc2c1CC1CC1] | 4-(3-(cyclopropylmethyl)-2-methyl-2H-indazol-5-yl)-5-fluoro-N-(5-(piperazin-1-ylmethyl)pyridin-2-yl)pyrimidin-2-amine |
| 16 | 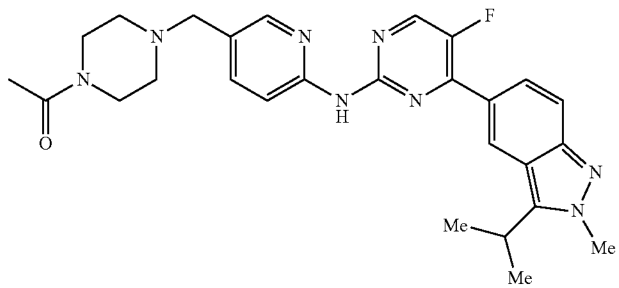 [SMILES: CC(=O)N1CCN(Cc2ccc(Nc3ncc(F)c(-c4ccc5nn(C)c(C(C)C)c5c4)n3)nc2)CC1] | 1-(4-((6-((5-fluoro-4-(3-isopropyl-2-methyl-2H-indazol-5-yl)pyrimidin-2-yl)amino)pyridin-3-yl)methyl)piperazin-1-yl)ethan-1-one |
| 17 | 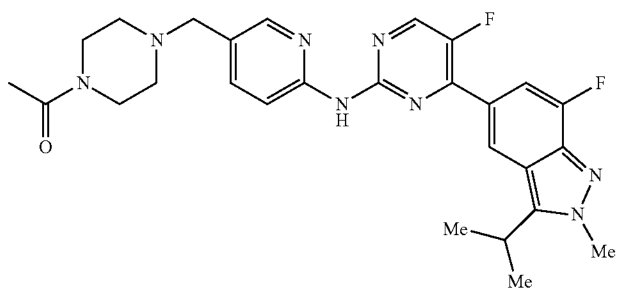 [SMILES: CC(=O)N1CCN(Cc2ccc(Nc3ncc(F)c(-c4cc(F)c5nn(C)c(C(C)C)c5c4)n3)nc2)CC1] | 1-(4-((6-((5-fluoro-4-(7-fluoro-3-isopropyl-2-methyl-2H-indazol-5-yl)pyrimidin-2-yl)amino)pyridin-3-yl)methyl)piperazin-1-yl)ethan-1-one |
| 18 | 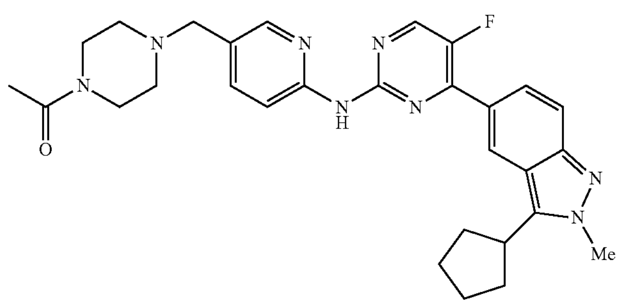 [SMILES: CC(=O)N1CCN(Cc2ccc(Nc3ncc(F)c(-c4ccc5nn(C)c(C6CCCC6)c5c4)n3)nc2)CC1] | 1-(4-((6-((4-(3-cyclopentyl-2-methyl-2H-indazol-5-yl)-5-fluoropyrimidin-2-yl)amino)pyridin-3-yl)methyl)piperazin-1-yl)ethan-1-one |
| 19 | 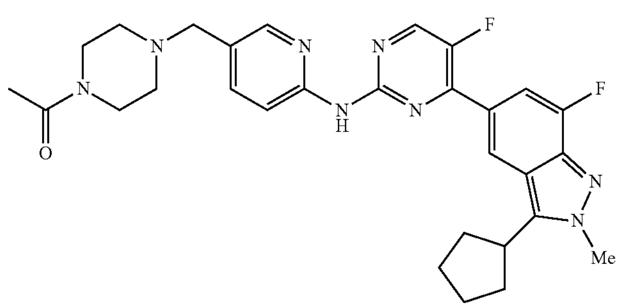 [SMILES: CC(=O)N1CCN(Cc2ccc(Nc3ncc(F)c(-c4cc(F)c5nn(C)c(C6CCCC6)c5c4)n3)nc2)CC1] | 1-(4-((6-((4-(3-cyclopentyl-7-fluoro-2-methyl-2H-indazol-5-yl)-5-fluoropyrimidin-2-yl)amino)pyridin-3-yl)methyl)piperazin-1-yl)ethan-1-one |

TABLE 1-continued

Selected examples of the compounds of formula (I)

| Example | Structure | Name |
| --- | --- | --- |
| 20 | 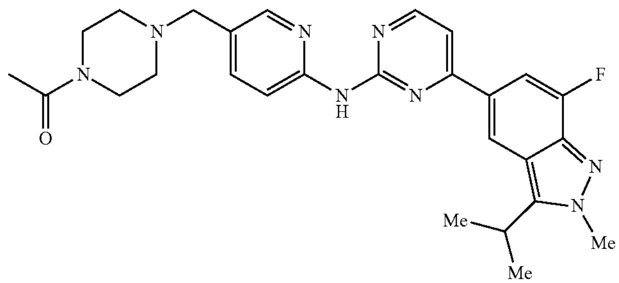 [SMILES: CC(=O)N1CCN(Cc2ccc(Nc3nccc(-c4cc(F)c5nn(C)c(C(C)C)c5c4)n3)nc2)CC1] | 1-(4-((6-((4-(7-fluoro-3-isopropyl-2-methyl-2H-indazol-5-yl)pyrimidin-2-yl)amino)pyridin-3-yl)methyl)piperazin-1-yl)ethan-1-one |
| 21 | 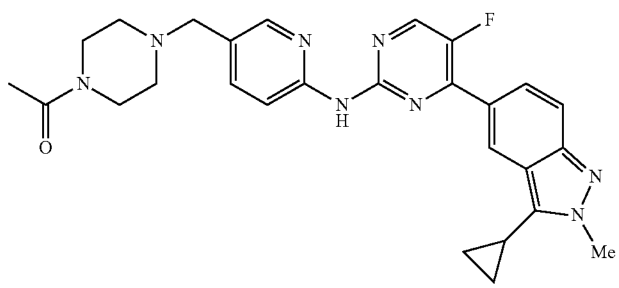 [SMILES: CC(=O)N1CCN(Cc2ccc(Nc3ncc(F)c(-c4ccc5nn(C)c(C6CC6)c5c4)n3)nc2)CC1] | 1-(4-((6-((4-(3-cyclopropyl-2-methyl-2H-indazol-5-yl)-5-fluoropyrimidin-2-yl)amino)pyridin-3-yl)methyl)piperazin-1-yl)ethan-1-one |
| 22 | 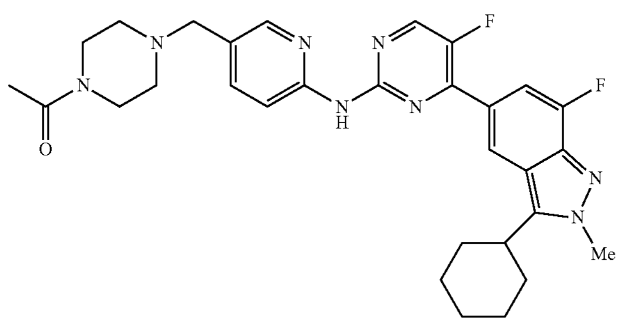 [SMILES: CC(=O)N1CCN(Cc2ccc(Nc3ncc(F)c(-c4cc(F)c5nn(C)c(C6CCCCC6)c5c4)n3)nc2)CC1] | 1-(4-((6-((4-(3-cyclohexyl-7-fluoro-2-methyl-2H-indazol-5-yl)-5-fluoropyrimidin-2-yl)amino)pyridin-3-yl)methyl)piperazin-1-yl)ethan-1-one |
| 23 | 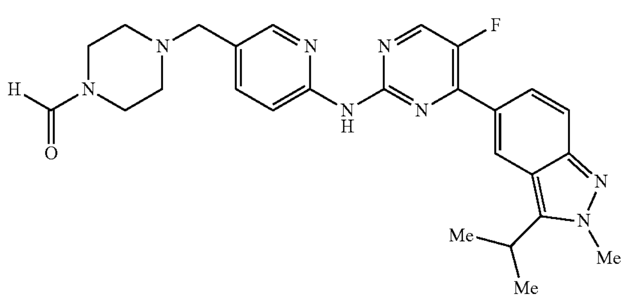 [SMILES: CC(C)c1c2cc(-c3nc(Nc4ccc(CN5CCN(C=O)CC5)cn4)ncc3F)ccc2nn1C] | 4-((6-((5-fluoro-4-(3-isopropyl-2-methyl-2H-indazol-5-yl)pyrimidin-2-yl)amino)pyridin-3-yl)methyl)piperazine-1-carbaldehyde |
| 24 | 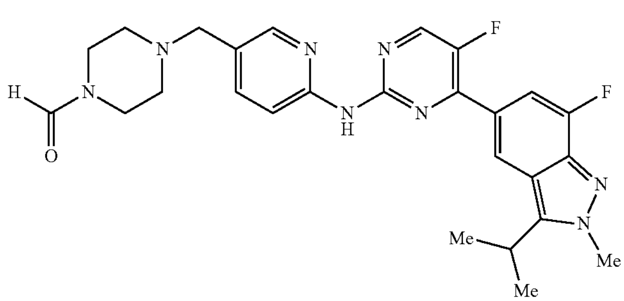 [SMILES: CC(C)c1c2cc(-c3nc(Nc4ccc(CN5CCN(C=O)CC5)cn4)ncc3F)cc(F)c2nn1C] | 4-((6-((5-fluoro-4-(7-fluoro-3-isopropyl-2-methyl-2H-indazol-5-yl)pyrimidin-2-yl)amino)pyridin-3-yl)methyl)piperazine-1-carbaldehyde |

TABLE 1-continued

Selected examples of the compounds of formula (I)

| Example | Structure | Name |
|---------|-----------|------|
| 25 | 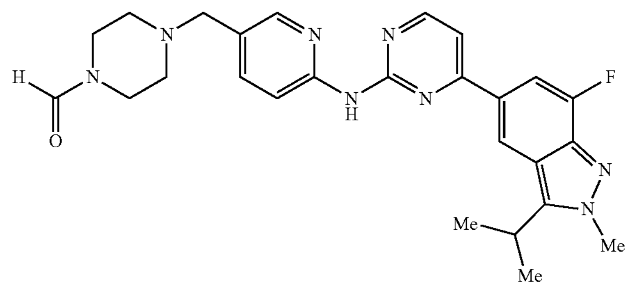 | 4-((6-((4-(7-fluoro-3-isopropyl-2-methyl-2H-indazol-5-yl)pyrimidin-2-yl)amino)pyridin-3-yl)methyl)piperazine-1-carbaldehyde |
| 26 | 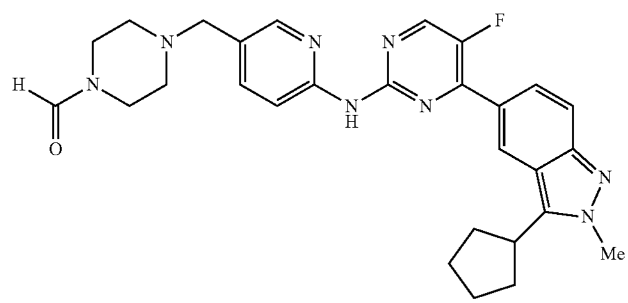 [SMILES: Cn1nc2ccc(-c3nc(Nc4ccc(CN5CCN(C=O)CC5)cn4)ncc3F)cc2c1C1CCCC1] | 4-((6-((4-(3-cyclopentyl-2-methyl-2H-indazol-5-yl)-5-fluoropyrimidin-2-yl)amino)pyridin-3-yl)methyl)piperazine-1-carbaldehyde |
| 27 | 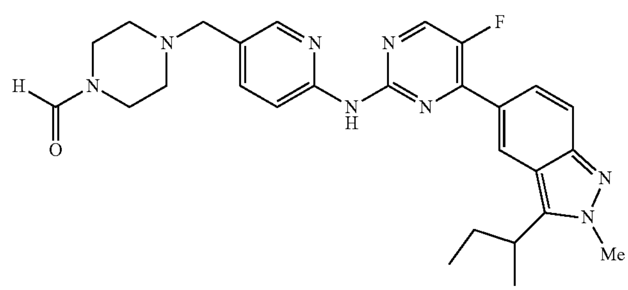 [SMILES: CCC(C)c1c2cc(-c3nc(Nc4ccc(CN5CCN(C=O)CC5)cn4)ncc3F)ccc2nn1C] | 4-((6-((4-(3-(sec-butyl)-2-methyl-2H-indazol-5-yl)-5-fluoropyrimidin-2-yl)amino)pyridin-3-yl)methyl)piperazine-1-carbaldehyde |
| 28 | 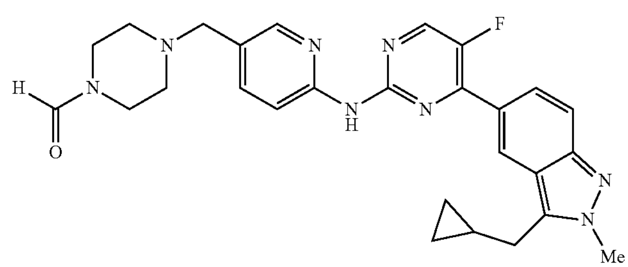 [SMILES: Cn1nc2ccc(-c3nc(Nc4ccc(CN5CCN(C=O)CC5)cn4)ncc3F)cc2c1CC1CC1] | 4-((6-((4-(3-(cyclopropylmethyl)-2-methyl-2H-indazol-5-yl)-5-fluoropyrimidin-2-yl)amino)pyridin-3-yl)methyl)piperazine-1-carbaldehyde |
| 29 | 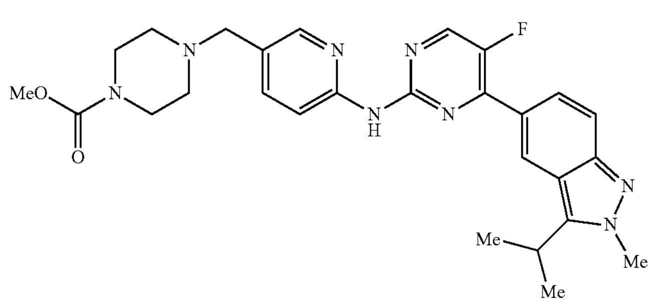 [SMILES: COC(=O)N1CCN(Cc2ccc(Nc3ncc(F)c(-c4ccc5nn(C)c(C(C)C)c5c4)n3)nc2)CC1] | methyl 4-((6-((5-fluoro-4-(3-isopropyl-2-methyl-2H-indazol-5-yl)pyrimidin-2-yl)amino)pyridin-3-yl)methyl)piperazine-1-carboxylate |

TABLE 1-continued

Selected examples of the compounds of formula (I)

| Example | Structure | Name |
|---|---|---|
| 30 | 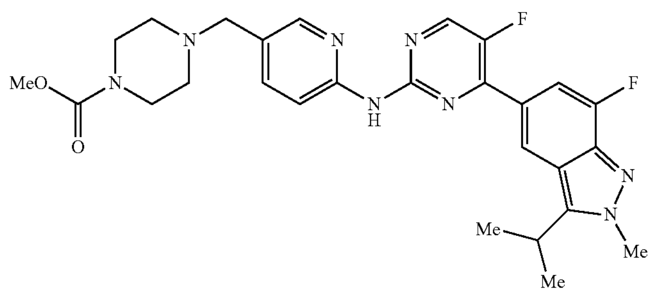 [SMILES: COC(=O)N1CCN(Cc2ccc(Nc3ncc(F)c(-c4cc(F)c5nn(C)c(C(C)C)c5c4)n3)nc2)CC1] | methyl 4-((6-((5-fluoro-4-(7-fluoro-3-isopropyl-2-methyl-2H-indazol-5-yl)pyrimidin-2-yl)amino)pyridin-3-yl)methyl)piperazine-1-carboxylate |
| 31 | 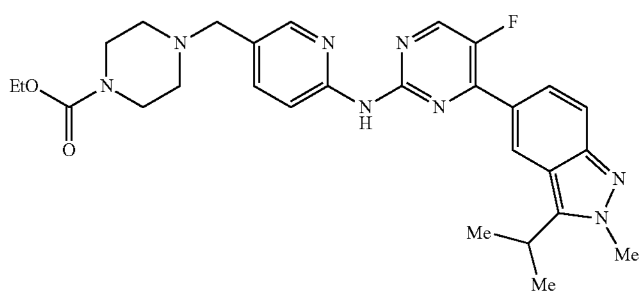 [SMILES: CCOC(=O)N1CCN(Cc2ccc(Nc3ncc(F)c(-c4ccc5nn(C)c(C(C)C)c5c4)n3)nc2)CC1] | ethyl 4-((6-((5-fluoro-4-(3-isopropyl-2-methyl-2H-indazol-5-yl)pyrimidin-2-yl)amino)pyridin-3-yl)methyl)piperazine-1-carboxylate |
| 32 | 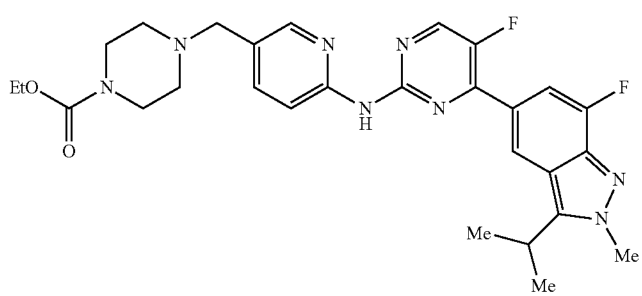 [SMILES: CCOC(=O)N1CCN(Cc2ccc(Nc3ncc(F)c(-c4cc(F)c5nn(C)c(C(C)C)c5c4)n3)nc2)CC1] | ethyl 4-((6-((5-fluoro-4-(7-fluoro-3-isopropyl-2-methyl-2H-indazol-5-yl)pyrimidin-2-yl)amino)pyridin-3-yl)methyl)piperazine-1-carboxylate |
| 33 | 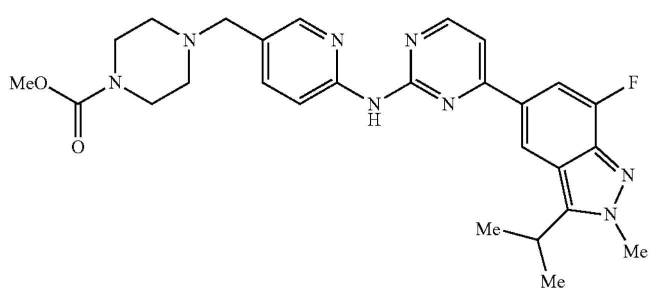 | methyl 4-((6-((4-(7-fluoro-3-isopropyl-2-methyl-2H-indazol-5-yl)pyrimidin-2-yl)amino)pyridin-3-yl)methyl)piperazine-1-carboxylate |
| 34 | 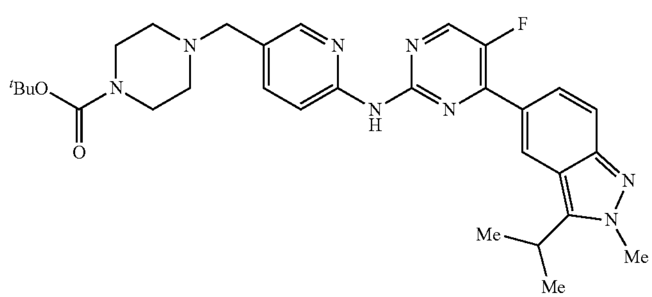 | tert-butyl 4-((6-((5-fluoro-4-(3-isopropyl-2-methyl-2H-indazol-5-yl)pyrimidin-2-yl)amino)pyridin-3-yl)methyl)piperazine-1-carboxylate |

TABLE 1-continued

Selected examples of the compounds of formula (I)

| Example | Structure | Name |
|---|---|---|
| 35 | 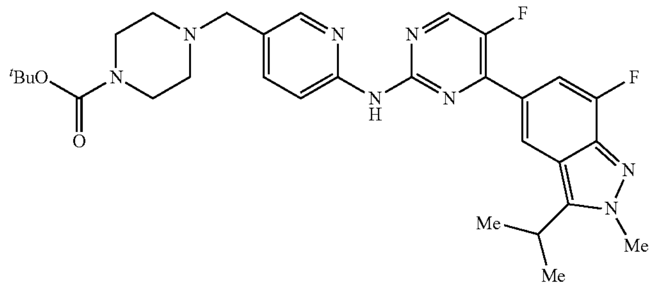 | tert-butyl 4-((6-((5-fluoro-4-(7-fluoro-3-isopropyl-2-methyl-2H-indazol-5-yl)pyrimidin-2-yl)amino)pyridin-3-yl)methyl)piperazine-1-carboxylate |
| 36 | 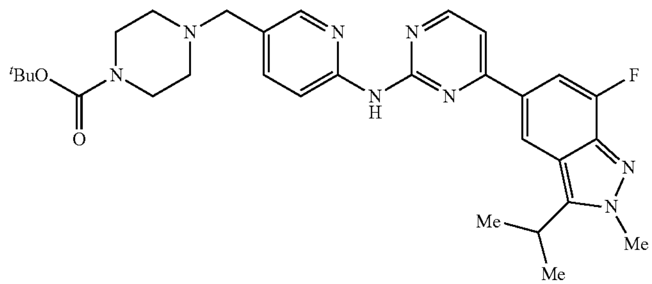 [SMILES: COC(=O)N1CCN(Cc2ccc(Nc3nccc(-c4cc(F)c5nn(C)c(C(C)C)c5c4)n3)nc2)CC1] | tert-butyl 4-((6-((4-(7-fluoro-3-isopropyl-2-methyl-2H-indazol-5-yl)pyrimidin-2-yl)amino)pyridin-3-yl)methyl)piperazine-1-carboxylate |

Biological Assays

Compounds of the formula (I) are novel CDK4/6 inhibitors that have been or can be evaluated for their activity according to the procedures described below, using compound 1.HCl to illustrate.

CDK4/cyclin D1, CDK4/cyclin D3, CDK6/cyclin D1, and CDK6/cyclin D3 were added to freshly prepared substrate solution (RB Protein, 3 μM) which was in freshly made reaction buffer (20 mM Hepes (pH 7.5), 10 mM $MgCl_2$, 1 mM EGTA, 0.02% Brij35, 0.02 mg/mL BSA, 0.1 mM $Na_3VO_4$, 2 mM DTT, 1% DMSO) and gently mixed, respectively. Compound 1.HCl was tested in a 10-dose $IC_{50}$ mode with 3-fold dilution starting at 0.1 μM. Compound 1.HCl was prepared and diluted in DMSO and was delivered into the kinases/substrate reaction mixture by Acoustic technology (Echo550; nanoliter range), then incubated for 20 min at room temperature. Then 33P-ATP (1 μM) was added into the reaction mixture to initiate the reaction. The kinase reaction was incubated at room temperature for 2 hours. The reactions were spotted onto P81 ion-exchange paper and radioactivity was detected by filter-binding method. The kinase activity data were expressed as the percent remaining kinase activity in test samples compared to vehicle (Dimethyl Sulfoxide) reactions. The compound's $IC_{50}$ values and curve fits for each kinase were obtained by fitting to a nonlinear regression curve with the "four parameter logistic equation" in Prism (GraphPad Softwere). Under the conditions, $IC_{50}$ values for 1. HCl were determined for all 4 kinases: CDK4/cyclin D1, CDK4/cyclin D3, CDK6/cyclin D1, and CDK6/cyclin D3 and are shown in Table 2, as compared with those of ethylated counterpart, namely N-(5-((4-ethylpiperazin-1-yl)methyl)pyridin-2-yl)-5-fluoro-4-(3-isopropyl-2-methyl-2H-indazol-5-yl)pyrimidin-2-amine, or compound 37. The results are comparable with, or in certain cases better than, those of compound 37. The significance of this discovery is that in principal compound 1 can be administered through various prodrug forms disclosed herein, which can be hydrolyzed under physiological conditions to generate active compound 1 in situ, in which 1 serves as a common active moiety, thus achieving controlled release for better targeting the diseases, in particular tumors.

TABLE 2

$IC_{50}$ values of compounds 1•HCl and 37 for CDK4/cyclin $D_1$, CDK4/cyclin $D_3$, CDK6/cyclin $D_1$, and CDK6/cyclin $D_3$.

| | Compounds ($IC_{50}$, M) | |
|---|---|---|
| Kinases | 1•HCl | 37 |
| CDK4/cyclin D1 | 7.05E-10 | 1.47E-09 |
| CDK4/cyclin D3 | 3.99E-09 | 1.98E-09 |
| CDK6/cyclin D1 | 1.11E-09 | 2.38E-08 |
| CDK6/cyclin D3 | 2.56E-08 | 5.66E-09 |

It will be understood by those of skill in the art that numerous and various modifications can be made to the compounds, compositions, and/or methods of the present invention without departing from the spirit of the invention. Therefore, the various embodiments of the present invention described herein are illustrative only, and are not intended to limit the scope of the invention in any way. All references cited herein are incorporated by reference in their entirety.

What is claimed is:

1. A compound of formula (I):

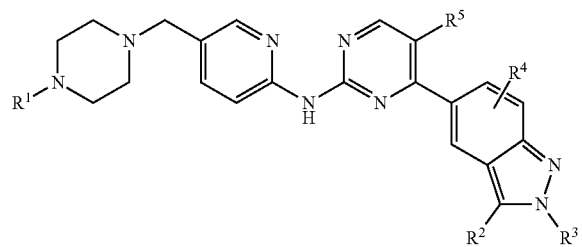

(I)

or a pharmaceutically acceptable salt or solvate thereof, wherein:

$R^1$ is hydrogen, —C(O)R or —C(O)OR', wherein R is hydrogen, $C_1$-$C_8$ alkyl, or $C_3$-$C_7$ cycloalkyl; and wherein R' is $C_1$-$C_8$ alkyl or $C_3$-$C_7$ cycloalkyl $R^2$ and $R^3$ are each independently hydrogen, $C_1$-$C_8$ alkyl, $C_3$-$C_7$ cycloalkyl, or $C_3$-$C_7$ cycloalkylmethyl;

$R^4$ is hydrogen, halogen, $C_1$-$C_8$ alkyl, or $C_3$-$C_7$ cycloalkyl; and $R^5$ is hydrogen or halogen.

2. The compound of claim 1, or a pharmaceutically acceptable salt or solvate thereof, wherein $R^1$ is C(O)R, wherein R is $C_1$-$C_6$ alkyl.

3. The compound of claim 1, or a pharmaceutically acceptable salt or solvate thereof, wherein $R^1$ is —C(O)R, wherein R is methyl, ethyl, propyl, or isopropyl.

4. The compound of claim 1, or a pharmaceutically acceptable salt or solvate thereof, wherein $R^2$ is $C_1$-$C_6$ alkyl, $C_3$-$C_6$ cycloalkyl, or $C_3$-$C_6$ cycloalkylmethyl.

5. The compound of claim 1, or a pharmaceutically acceptable salt or solvate thereof, wherein $R^2$ is methyl, ethyl, propyl, isopropyl, cyclopropyl, cyclopentyl, cyclopropylmethyl, or cyclopentylmethyl.

6. The compound of claim 1, or a pharmaceutically acceptable salt or solvate thereof, wherein $R^3$ is $C_1$-$C_6$ alkyl or $C_3$-$C_6$ cycloalkyl.

7. The compound of claim 1, or a pharmaceutically acceptable salt or solvate thereof, wherein $R^3$ is methyl, ethyl, propyl, isopropyl, or cyclopropyl.

8. The compound of claim 1, or a pharmaceutically acceptable salt or solvate thereof, wherein $R^4$ is hydrogen or halogen located at the 7-position of the indazole ring, characterized by formula Ia:

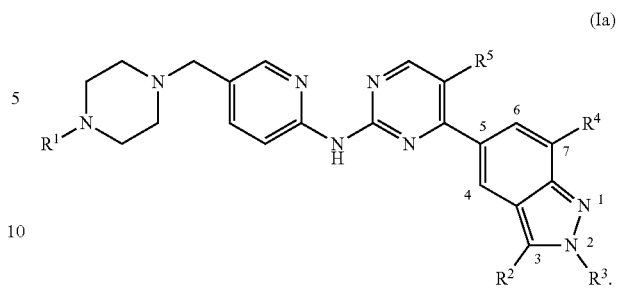

(Ia)

9. The compound of claim 1, or a pharmaceutically acceptable salt or solvate thereof, wherein $R^5$ is hydrogen or fluoro.

10. The compound of claim 1, or a pharmaceutically acceptable salt or solvate thereof, wherein $R^1$ is —C(O)R, wherein R is methyl or ethyl; $R^2$ is isopropyl, cyclopropyl, cyclopropylmethyl, or cyclopentyl; $R^3$ is methyl or ethyl; $R^4$ is hydrogen or fluoro; and $R^5$ is hydrogen or fluoro.

11. The compound of claim 10, or a pharmaceutically acceptable salt or solvate thereof, selected from the group consisting of:

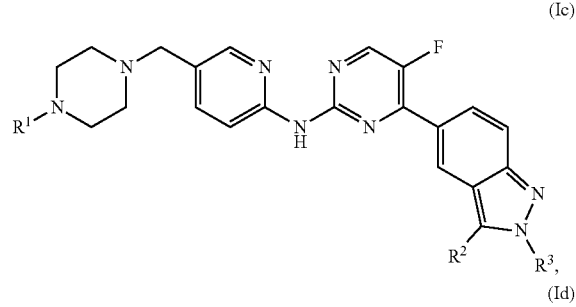

(Ic)

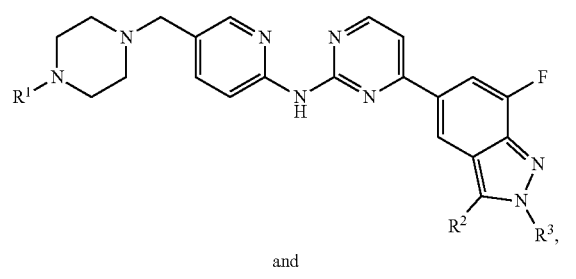

(Id)

and

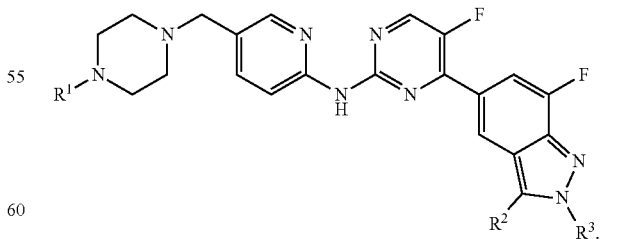

(Ie)

12. The compound of claim 11, wherein $R^1$ is $CH_3C(O)$—; $R^2$ is isopropyl; and $R^3$ is methyl.

13. A compound or a pharmaceutically acceptable salt or solvate thereof, selected from the list in the table below:

| Example | Structure | Name |
|---|---|---|
| 1 | 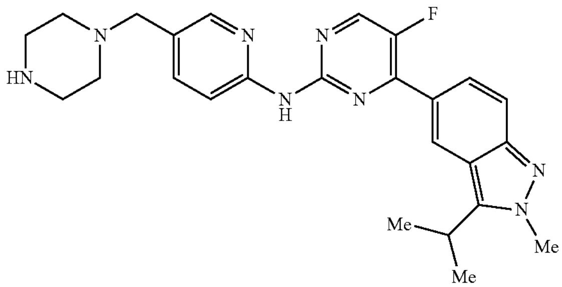 [SMILES: CC(C)c1c2cc(-c3nc(Nc4ccc(CN5CCNCC5)cn4)ncc3F)ccc2nn1C] | 5-fluoro-4-(3-isopropyl-2-methyl-2H-indazol-5-yl)-N-(5-(piperazin-1-ylmethyl)pyridin-2-yl)pyrimidin-2-amine |
| 2 | 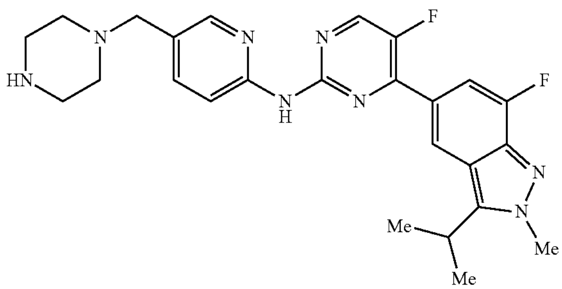 [SMILES: CC(C)c1c2cc(-c3nc(Nc4ccc(CN5CCNCC5)cn4)ncc3F)cc(F)c2nn1C] | 5-fluoro-4-(7-fluoro-3-isopropyl-2-methyl-2H-indazol-5-yl)-N-(5-(piperazin-1-ylmethyl)pyridin-2-yl)pyrimidin-2-amine |
| 3 | 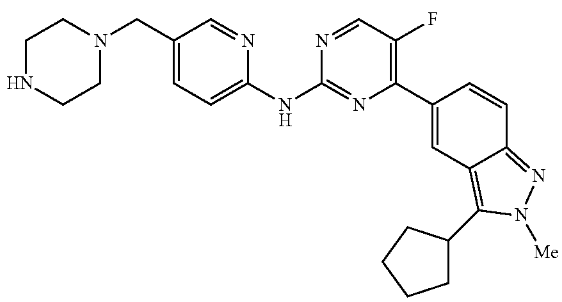 [SMILES: Cn1nc2ccc(-c3nc(Nc4ccc(CN5CCNCC5)cn4)ncc3F)cc2c1C1CCCC1] | 4-(3-cyclopentyl-2-methyl-2H-indazol-5-yl)-5-fluoro-N-(5-(piperazin-1-ylmethyl)pyridin-2-yl)pyrimidin-2-amine |
| 4 | 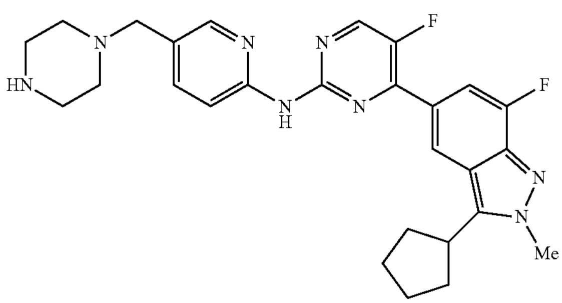 [SMILES: Cn1nc2c(F)cc(-c3nc(Nc4ccc(CN5CCNCC5)cn4)ncc3F)cc2c1C1CCCC1] | 4-(3-cyclopentyl-7-fluoro-2-methyl-2H-indazol-5-yl)-5-fluoro-N-(5-(piperazin-1-ylmethyl)pyridin-2-yl)pyrimidin-2-amine |
| 5 | 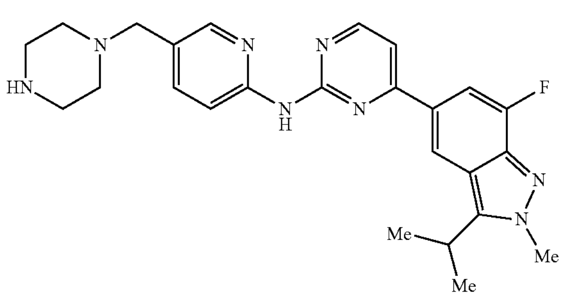 [SMILES: CC(C)c1c2cc(-c3ccnc(Nc4ccc(CN5CCNCC5)cn4)n3)cc(F)c2nn1C] | 4-(7-fluoro-3-isopropyl-2-methyl-2H-indazol-5-yl)-N-(5-(piperazin-1-ylmethyl)pyridin-2-yl)pyrimidin-2-amine |

-continued

| Example | Structure | Name |
|---|---|---|
| 6 | 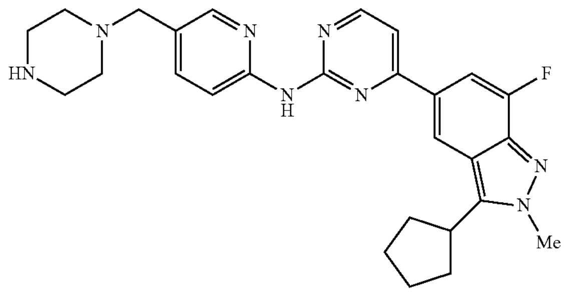 [SMILES: Cn1nc2c(F)cc(-c3ccnc(Nc4ccc(CN5CCNCC5)cn4)n3)cc2c1C1CCCC1] | 4-(3-cyclopentyl-7-fluoro-2-methyl-2H-indazol-5-yl)-N-(5-(piperazin-1-ylmethyl)pyridin-2-yl)pyrimidin-2-amine |
| 7 | 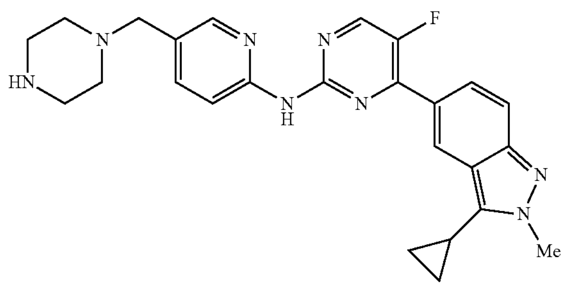 [SMILES: Cn1nc2ccc(-c3nc(Nc4ccc(CN5CCNCC5)cn4)ncc3F)cc2c1C1CC1] | 4-(3-cyclopropyl-2-methyl-2H-indazol-5-yl)-5-fluoro-N-(5-(piperazin-1-ylmethyl)pyridin-2-yl)pyrimidin-2-amine |
| 8 | 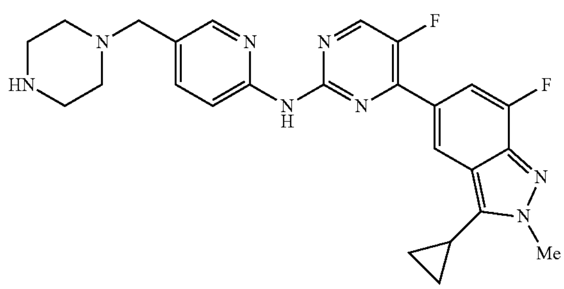 [SMILES: Cn1nc2c(F)cc(-c3nc(Nc4ccc(CN5CCNCC5)cn4)ncc3F)cc2c1C1CC1] | 4-(3-cyclopropyl-7-fluoro-2-methyl-2H-indazol-5-yl)-5-fluoro-N-(5-(piperazin-1-ylmethyl)pyridin-2-yl)pyrimidin-2-amine |
| 9 | 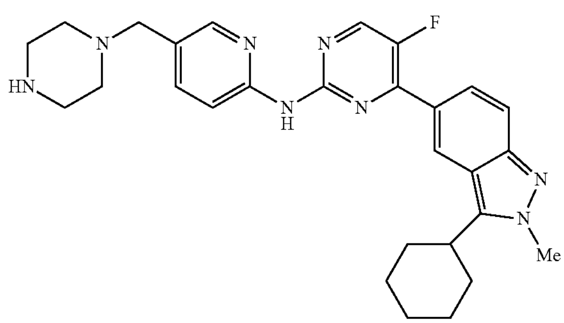 [SMILES: Cn1nc2ccc(-c3nc(Nc4ccc(CN5CCNCC5)cn4)ncc3F)cc2c1C1CCCCC1] | 4-(3-cyclohexyl-2-methyl-2H-indazol-5-yl)-5-fluoro-N-(5-(piperazin-1-ylmethyl)pyridin-2-yl)pyrimidin-2-amine |
| 10 | 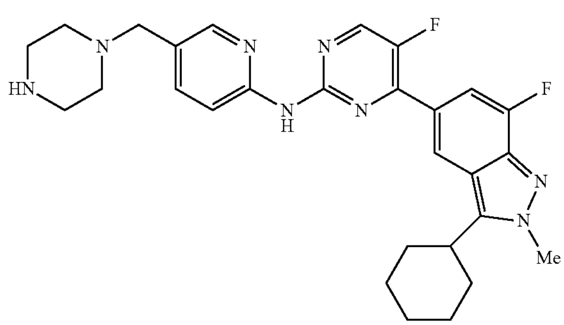 [SMILES: Cn1nc2c(F)cc(-c3nc(Nc4ccc(CN5CCNCC5)cn4)ncc3F)cc2c1C1CCCCC1] | 4-(3-cyclohexyl-7-fluoro-2-methyl-2H-indazol-5-yl)-5-fluoro-N-(5-(piperazin-1-ylmethyl)pyridin-2-yl)pyrimidin-2-amine |

-continued

| Example | Structure | Name |
|---|---|---|
| 11 | 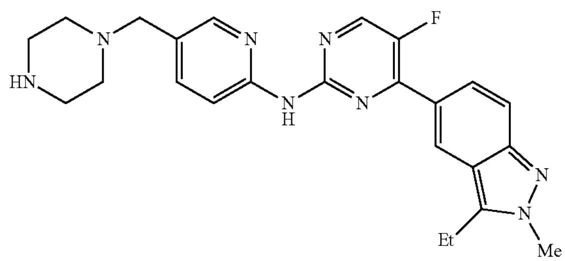 [SMILES: CCc1c2cc(-c3nc(Nc4ccc(CN5CCNCC5)cn4)ncc3F)ccc2nn1C] | 4-(3-ethyl-2-methyl-2H-indazol-5-yl)-5-fluoro-N-(5-(piperazin-1-ylmethyl)pyridin-2-yl)pyrimidin-2-amine |
| 12 | 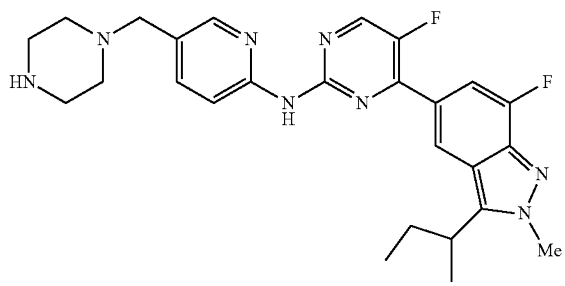 [SMILES: CCC(C)c1c2cc(-c3nc(Nc4ccc(CN5CCNCC5)cn4)ncc3F)cc(F)c2nn1C] | 4-(3-(sec-butyl)-7-fluoro-2-methyl-2H-indazol-5-yl)-5-fluoro-N-(5-(piperazin-1-ylmethyl)pyridin-2-yl)pyrimidin-2-amine |
| 13 | 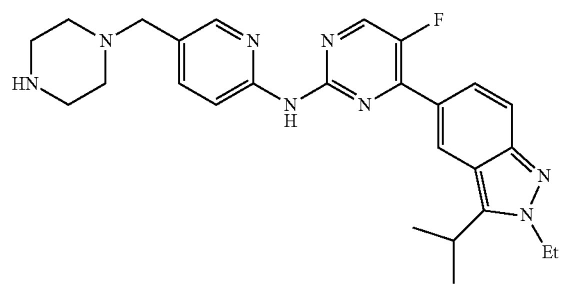 [SMILES: CCn1nc2ccc(-c3nc(Nc4ccc(CN5CCNCC5)cn4)ncc3F)cc2c1C(C)C] | 4-(2-ethyl-3-isopropyl-2H-indazol-5-yl)-5-fluoro-N-(5-(piperazin-1-ylmethyl)pyridin-2-yl)pyrimidin-2-amine |
| 14 | 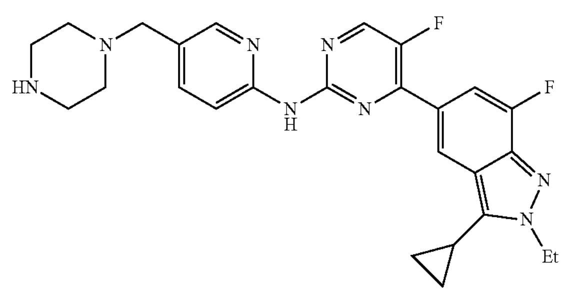 [SMILES: CCn1nc2c(F)cc(-c3nc(Nc4ccc(CN5CCNCC5)cn4)ncc3F)cc2c1C1CC1] | 4-(3-cyclopropyl-2-ethyl-7-fluoro-2H-indazol-5-yl)-5-fluoro-N-(5-(piperazin-1-ylmethyl)pyridin-2-yl)pyrimidin-2-amine |
| 15 | 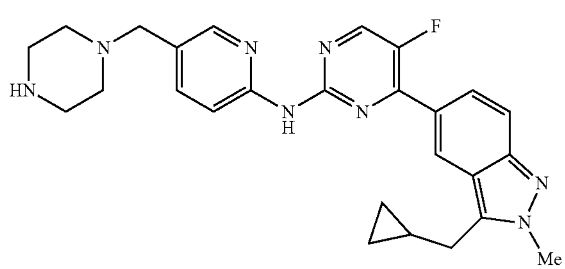 [SMILES: Cn1nc2ccc(-c3nc(Nc4ccc(CN5CCNCC5)cn4)ncc3F)cc2c1CC1CC1] | 4-(3-(cyclopropylmethyl)-2-methyl-2H-indazol-5-yl)-5-fluoro-N-(5-(piperazin-1-ylmethyl)pyridin-2-yl)pyrimidin-2-amine |

-continued

| Example | Structure | Name |
|---|---|---|
| 16 | 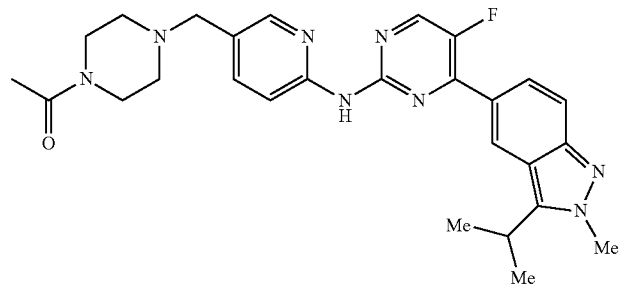 [SMILES: CC(=O)N1CCN(Cc2ccc(Nc3ncc(F)c(-c4ccc5nn(C)c(C(C)C)c5c4)n3)nc2)CC1] | 1-(4-((6-((5-fluoro-4-(3-isopropyl-2-methyl-2H-indazol-5-yl)pyrimidin-2-yl)amino)pyridin-3-yl)methyl)piperazin-1-yl)ethan-1-one |
| 17 | 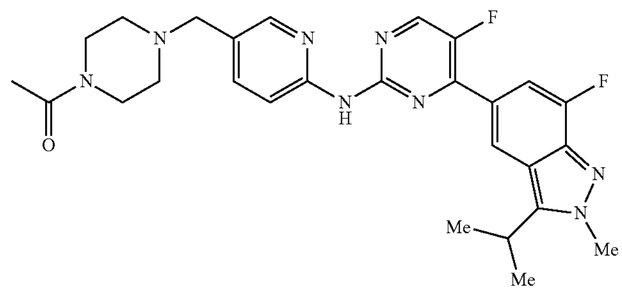 [SMILES: CC(=O)N1CCN(Cc2ccc(Nc3ncc(F)c(-c4cc(F)c5nn(C)c(C(C)C)c5c4)n3)nc2)CC1] | 1-(4-((6-((5-fluoro-4-(7-fluoro-3-isopropyl-2-methyl-2H-indazol-5-yl)pyrimidin-2-yl)amino)pyridin-3-yl)methyl)piperazin-1-yl)ethan-1-one |
| 18 | 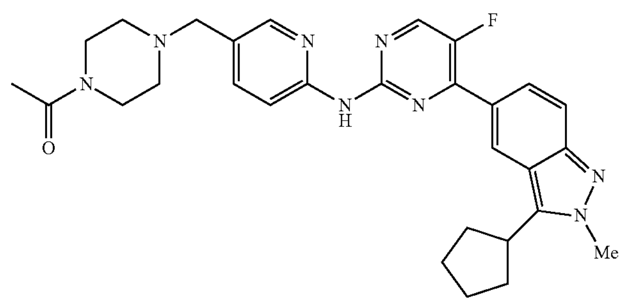 [SMILES: CC(=O)N1CCN(Cc2ccc(Nc3ncc(F)c(-c4ccc5nn(C)c(C6CCCC6)c5c4)n3)nc2)CC1] | 1-(4-((6-((4-(3-cyclopentyl-2-methyl-2H-indazol-5-yl)-5-fluoropyrimidin-2-yl)amino)pyridin-3-yl)methyl)piperazin-1-yl)ethan-1-one |
| 19 | 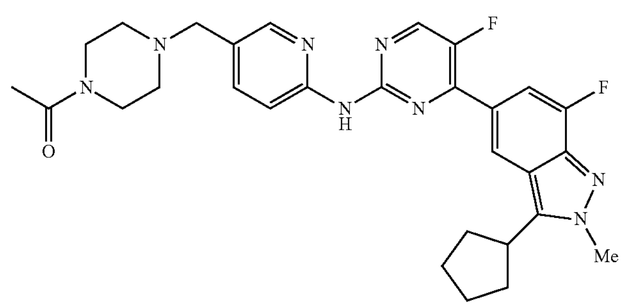 [SMILES: CC(=O)N1CCN(Cc2ccc(Nc3ncc(F)c(-c4cc(F)c5nn(C)c(C6CCCC6)c5c4)n3)nc2)CC1] | 1-(4-((6-((4-(3-cyclopentyl-7-fluoro-2-methyl-2H-indazol-5-yl)-5-fluoropyrimidin-2-yl)amino)pyridin-3-yl)methyl)piperazin-1-yl)ethan-1-one |
| 20 | 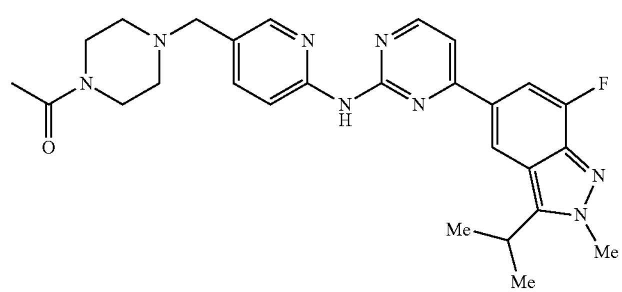 [SMILES: CC(=O)N1CCN(Cc2ccc(Nc3nccc(-c4cc(F)c5nn(C)c(C(C)C)c5c4)n3)nc2)CC1] | 1-(4-((6-((4-(7-fluoro-3-isopropyl-2-methyl-2H-indazol-5-yl)pyrimidin-2-yl)amino)pyridin-3-yl)methyl)piperazin-1-yl)ethan-1-one |

| Example | Structure | Name |
|---|---|---|
| 21 | 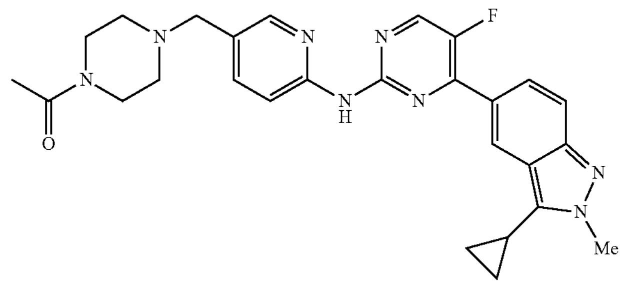 [SMILES: CC(=O)N1CCN(Cc2ccc(Nc3ncc(F)c(-c4ccc5nn(C)c(C6CC6)c5c4)n3)nc2)CC1] | 1-(4-((6-((4-(3-cyclopropyl-2-methyl-2H-indazol-5-yl)-5-fluoropyrimidin-2-yl)amino)pyridin-3-yl)methyl)piperazin-1-yl)ethan-1-one |
| 22 | 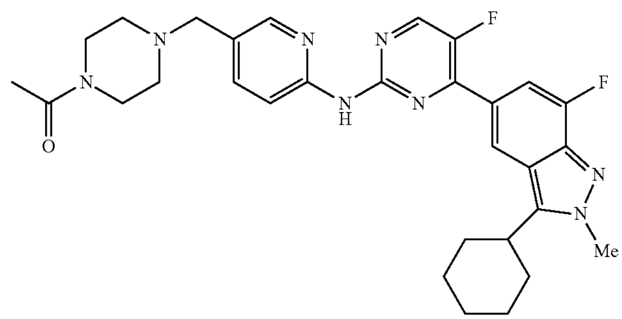 [SMILES: CC(=O)N1CCN(Cc2ccc(Nc3ncc(F)c(-c4cc(F)c5nn(C)c(C6CCCCC6)c5c4)n3)nc2)CC1] | 1-(4-((6-((4-(3-cyclohexyl-7-fluoro-2-methyl-2H-indazol-5-yl)-5-fluoropyrimidin-2-yl)amino)pyridin-3-yl)methyl)piperazin-1-yl)ethan-1-one |
| 23 | 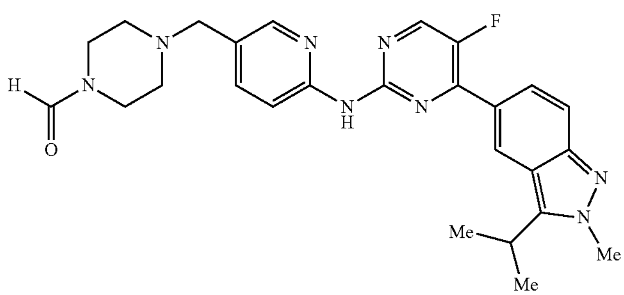 [SMILES: CC(C)c1c2cc(-c3nc(Nc4ccc(CN5CCN(C=O)CC5)cn4)ncc3F)ccc2nn1C] | 4-((6-((5-fluoro-4-(3-isopropyl-2-methyl-2H-indazol-5-yl)pyrimidin-2-yl)amino)pyridin-3-yl)methyl)piperazine-1-carbaldehyde |
| 24 | 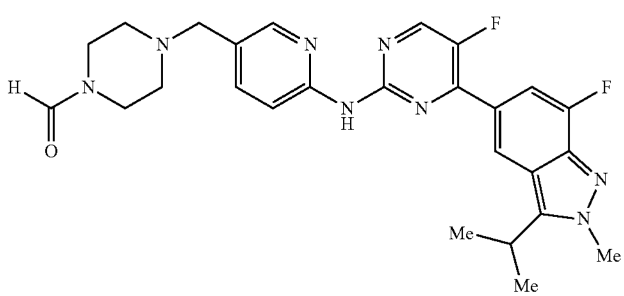 [SMILES: CC(C)c1c2cc(-c3nc(Nc4ccc(CN5CCN(C=O)CC5)cn4)ncc3F)cc(F)c2nn1C] | 4-((6-((5-fluoro-4-(7-fluoro-3-isopropyl-2-methyl-2H-indazol-5-yl)pyrimidin-2-yl)amino)pyridin-3-yl)methyl)piperazine-1-carbaldehyde |
| 25 | 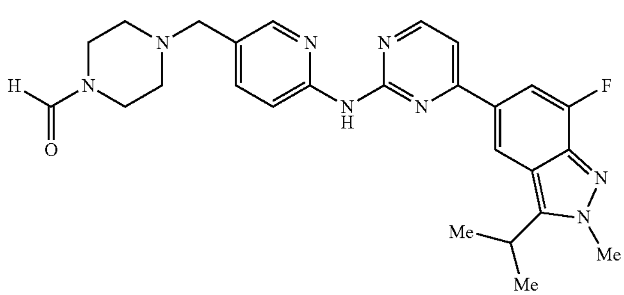 | 4-((6-((4-(7-fluoro-3-isopropyl-2-methyl-2H-indazol-5-yl)pyrimidin-2-yl)amino)pyridin-3-yl)methyl)piperazine-1-carbaldehyde |

-continued

| Example | Structure | Name |
|---|---|---|
| 26 | 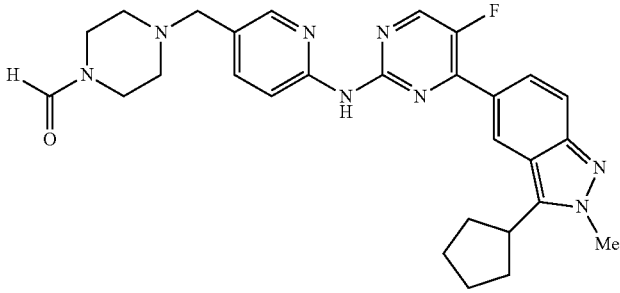 [SMILES: Cn1nc2ccc(-c3nc(Nc4ccc(CN5CCN(C=O)CC5)cn4)ncc3F)cc2c1C1CCCC1] | 4-((6-((4-(3-cyclopentyl-2-methyl-2H-indazol-5-yl)-5-fluoropyrimidin-2-yl)amino)pyridin-3-yl)methyl)piperazine-1-carbaldehyde |
| 27 | 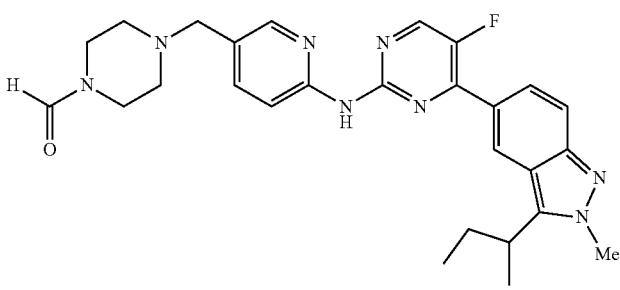 [SMILES: CCC(C)c1c2cc(-c3nc(Nc4ccc(CN5CCN(C=O)CC5)cn4)ncc3F)ccc2nn1C] | 4-((6-((4-(3-(sec-butyl)-2-methyl-2H-indazol-5-yl)-5-fluoropyrimidin-2-yl)amino)pyridin-3-yl)methyl)piperazine-1-carbaldehyde |
| 28 | 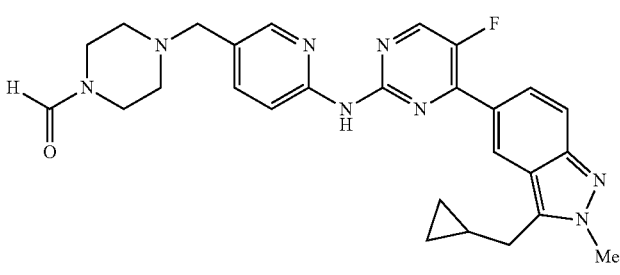 [SMILES: Cn1nc2ccc(-c3nc(Nc4ccc(CN5CCN(C=O)CC5)cn4)ncc3F)cc2c1CC1CC1] | 4-((6-((4-(3-(cyclopropylmethyl)-2-methyl-2H-indazol-5-yl)-5-fluoropyrimidin-2-yl)amino)pyridin-3-yl)methyl)piperazine-1-carbaldehyde |
| 29 | 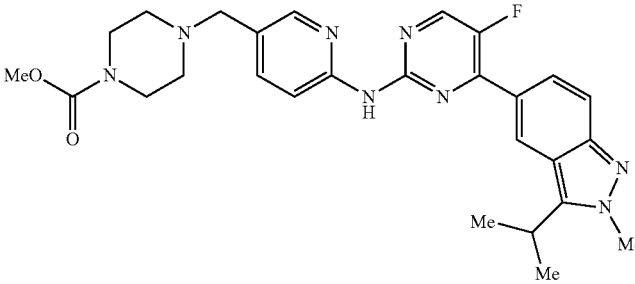 | methyl 4-((6-((5-fluoro-4-(3-isopropyl-2-methyl-2H-indazol-5-yl)pyrimidin-2-yl)amino)pyridin-3-yl)methyl)piperazine-1-carboxylate |
| 30 | 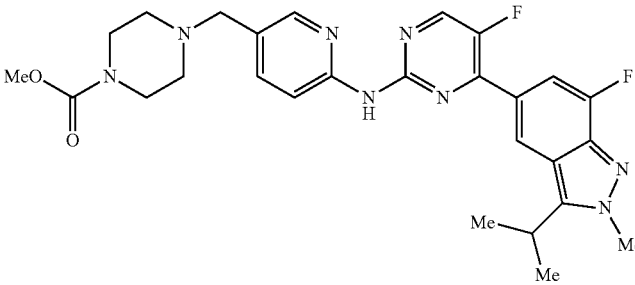 | methyl 4-((6-((5-fluoro-4-(7-fluoro-3-isopropyl-2-methyl-2H-indazol-5-yl)pyrimidin-2-yl)amino)pyridin-3-yl)methyl)piperazine-1-carboxylate |

-continued

| Example | Structure | Name |
|---|---|---|
| 31 | 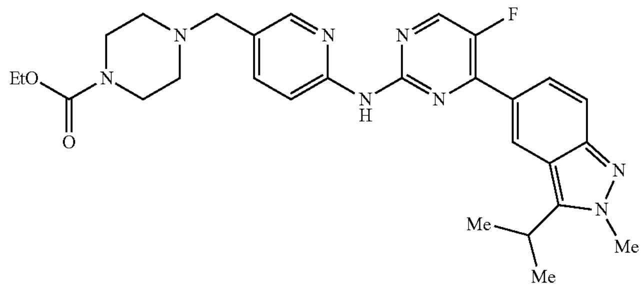 | ethyl 4-((6-((5-fluoro-4-(3-isopropyl-2-methyl-2H-indazol-5-yl)pyrimidin-2-yl)amino)pyridin-3-yl)methyl)piperazine-1-carboxylate |
| 32 | 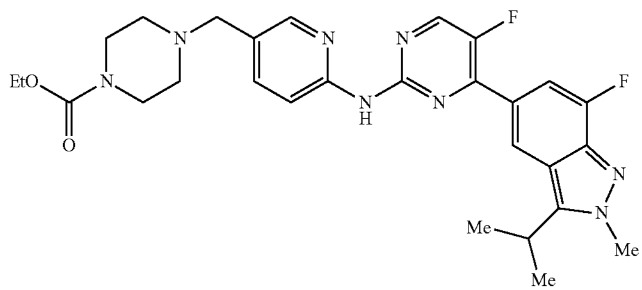 | ethyl 4-((6-((5-fluoro-4-(7-fluoro-3-isopropyl-2-methyl-2H-indazol-5-yl)pyrimidin-2-yl)amino)pyridin-3-yl)methyl)piperazine-1-carboxylate |
| 33 | 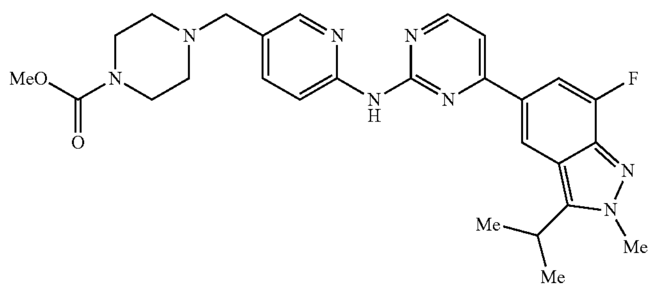 | methyl 4-((6-((4-(7-fluoro-3-isopropyl-2-methyl-2H-indazol-5-yl)pyrimidin-2-yl)amino)pyridin-3-yl)methyl)piperazine-1-carboxylate |
| 34 | 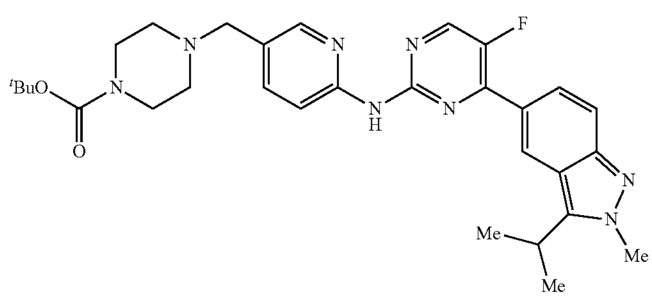 [SMILES: COC(=O)N1CCN(Cc2ccc(Nc3ncc(F)c(-c4ccc5nn(C)c(C(C)C)c5c4)n3)nc2)CC1] | tert-butyl 4-((6-((5-fluoro-4-(3-isopropyl-2-methyl-2H-indazol-5-yl)pyrimidin-2-yl)amino)pyridin-3-yl)methyl)piperazine-1-carboxylate |
| 35 | 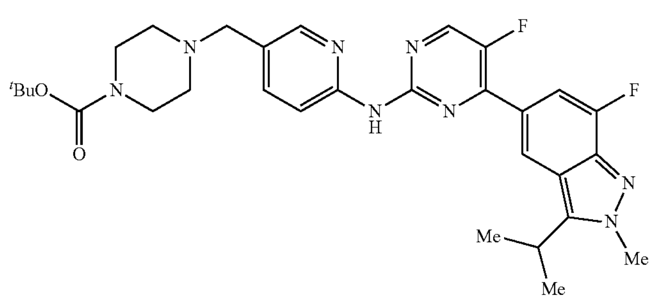 [SMILES: COC(=O)N1CCN(Cc2ccc(Nc3ncc(F)c(-c4cc(F)c5nn(C)c(C(C)C)c5c4)n3)nc2)CC1] | tert-butyl 4-((6-((5-fluoro-4-(7-fluoro-3-isopropyl-2-methyl-2H-indazol-5-yl)pyrimidin-2-yl)amino)pyridin-3-yl)methyl)piperazine-1-carboxylate |

| Example | Structure | Name |
|---------|-----------|------|
| 36 | 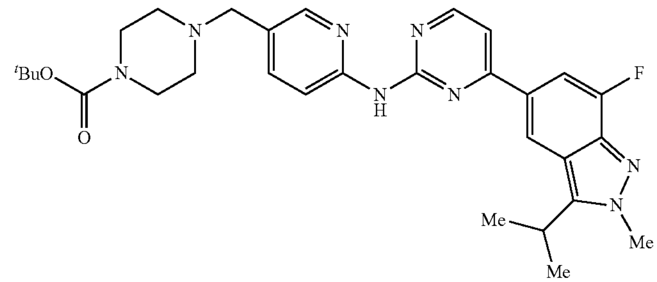 [SMILES: COC(=O)N1CCN(Cc2ccc(Nc3nccc(-c4cc(F)c5nn(C)c(C(C)C)c5c4)n3)nc2)CC1] | tert-butyl 4-((6-((4-(7-fluoro-3-isopropyl-2-methyl-2H-indazol-5-yl)pyrimidin-2-yl)amino)pyridin-3-yl)methyl)piperazine-1-carboxylate. |

14. A pharmaceutical composition comprising a compound of claim 1, or a pharmaceutically acceptable salt or solvate thereof, and one or more pharmaceutically acceptable adjuvants, diluents, and/or carriers.

15. A method of treating a disease, disorder, or condition mediated through activity of cyclin-dependent kinase (CDK) 4, CDK 6, or combination thereof, comprising administering to a subject in need thereof a therapeutically effective amount of the compound of claim 1.

16. The method of claim 15, wherein said disease or disorder is selected from the group consisting of colorectal cancer, breast cancer, lung cancer, especially non-small cell lung cancer (NSCLC), prostate cancer, glioblastoma, mantel cell lymphoma (MCL), chronic myeloid leukemia (CIVIL), acute myeloid leukemia (AML), arthritis, and cystic fibrosis.

17. The method of claim 15, in combination with administering to said subject a second therapeutic agent.

18. The method of claim 17, wherein said second therapeutic agent is a different CDK inhibitor, HER2 inhibitor, mTOR inhibitor, or EGFR inhibitor.

19. A method of preparing a compound of formula (I), comprising a step of coupling intermediate E with intermediate G:

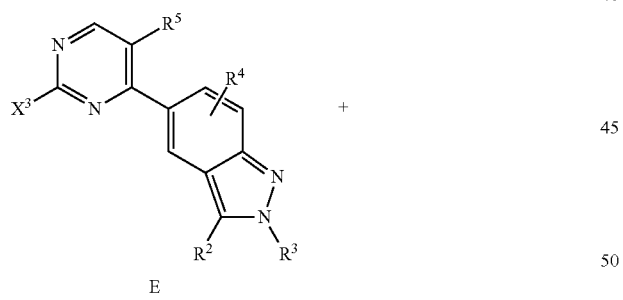

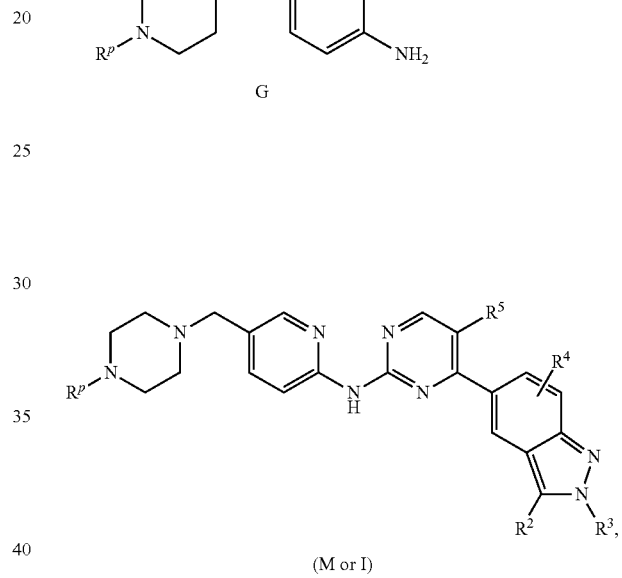

wherein $R^P$ is a protecting group or the same as $R^1$;

wherein when $R^P$ is a protecting group, the method further comprises removal of $R^P$ through base and/or acid mediated hydrolysis to form the compound of formula (Iaa):

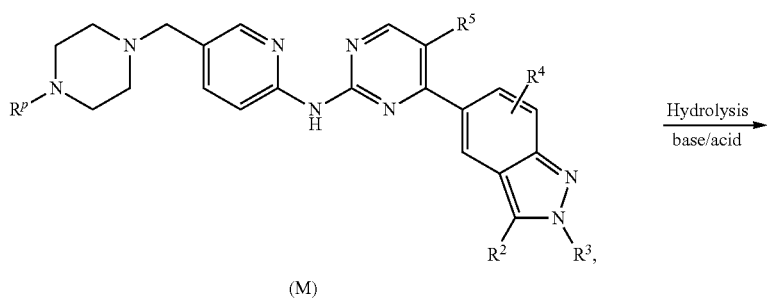

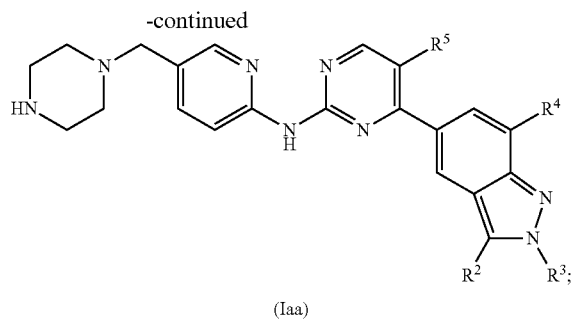
(Iaa)
and reaction of the compound (Iaa) with an acylating agent $R^1X^4$ to form (I), wherein $R^1$ is RC(O)— or R'OC(O)—, and $X^4$ is Cl or Br:
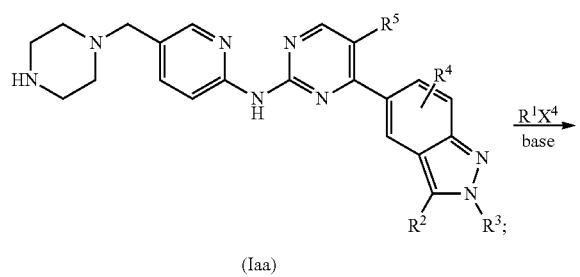
(Iaa)
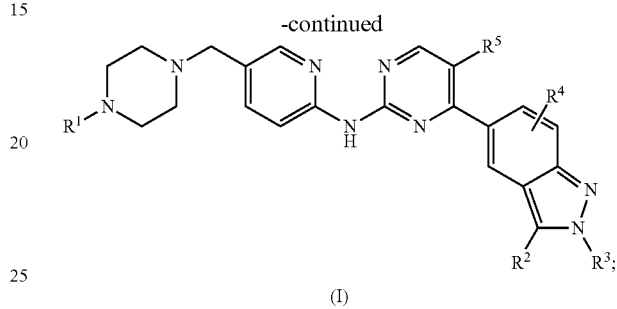
(I)
and R, R', and $R^2$ through $R^5$ are each independently defined as in claim 1, and $X^3$ is Cl, Br, or I.
* * * * *